US006586206B1

(12) United States Patent
Dixit et al.

(10) Patent No.: US 6,586,206 B1
(45) Date of Patent: Jul. 1, 2003

(54) METHODS FOR MAKING RECOMBINANT PROTEINS USING APOPTOSIS INHIBITORS

(75) Inventors: Vishva Dixit, Los Altos Hills, CA (US); Robert W. Hamilton, San Carlos, CA (US); Jana van de Goor, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/668,924

(22) Filed: Sep. 25, 2000

Related U.S. Application Data
(60) Provisional application No. 60/156,232, filed on Sep. 27, 1999.

(51) Int. Cl.$^7$ .............................. C12P 21/00; C12N 5/10; C12N 15/87
(52) U.S. Cl. ..................... 435/69.1; 435/69.2; 435/325; 435/358; 435/465
(58) Field of Search .............................. 435/69.1, 69.2, 435/325, 358, 465; 935/33, 44

(56) References Cited

U.S. PATENT DOCUMENTS 6,072,047 A    6/2000    Rauch et al. ............... 536/23.5

FOREIGN PATENT DOCUMENTS

| WO | WO 93/16192 | 8/1993 |
| WO | WO 97/44443 | 11/1997 |
| WO | WO 97/44444 | 11/1997 |
| WO | WO 98/10778 | 3/1998 |
| WO | WO 98/35986 | 8/1998 |
| WO | WO 01/18185 | 3/2001 |

OTHER PUBLICATIONS

Al–Rubeal and Singh, "Apoptosis in cell culture" *Curr. Opin. Biotech.* 9:152–156 (1998).
Ashkenazi and Dixit, "Death receptors: signaling and modulation" *Science* 281(5381):1305–1308 (1998).
Baldwin, A., "The NF–κB and IκB Proteins: New Discoveries and Insights" *Ann. Rev. Immunol.* 14:649–683 (1996).
Barr and Tomei, "Apoptosis and Its Role in Human Disease" *Bio/Technology* 12:487–493 (1994).
Beidler et al., "The Baculovirus p35 Protein Inhibits Fas– and Tumor Necrosis Factor–induced Apoptosis" *Journal of Biological Chemistry* 270:16526–16528 (1995).
Boldin et al., "Involvement of Mach, a Novel MORT1/FADD–Interacting Protease, in Fas/APO–1– and TNF Receptor–Induced Cell Death" *Cell* 85:803–815 (1996).
Boldin et al., "Self–Association of the "Death Domains" of the p55 Tumor Necrosis Factor (TNF) Receptor and Fas/APO1 Prompts Signaling for TNF and Fas/APO1 Effects" *Journal of Biological Chemistry* 270:387–391 (1995).
Chinnaiyan and Dixit, "The Cell–Death Machine" *Current Biology* 6:555–562 (1996).

Chinnaiyan et al., "FADD, a novel death domain–containing protein, interacts with the death domain of Fas and initiates apoptosis" *Cell* 81:505–512 (1995).
Chinnaiyan et al., "FADD/MORT1 Is a Common Mediator of CD95 (Fas/APO–1) and Tumor Necrosis Factor Receptor–induced Apoptisis" *Journal of Biological Chemistry* 271:4961–4965 (1996).
Chinnaiyan et al., "Interaction of CED–4 with CED–3 and CED–9: A Molecular Framework for Cell Death" *Science* 275:1122–1126 (1997).
Clem et al., "Prevention of Apoptosis by Baculovirus Gene During Infection of Insect Cells" *Science* 254:1388–1390 (1991).
Cleveland and Ihle, "Contenders in FasL/TNF Death Signaling" *Cell* 81:479–482 (1995).
Dickson, A. J., "Apoptosis regulation and its applications to biotechnology" *TIBTECH* 16:339–342 (1998).
Duan et al., "ICE–LAP6, a Novel Member of the ICE–Ced–3 Gene Family, Is Activated by the Cytotoxic T Cell Protease Granzyme B" *Journal of Biological Chemistry* 271(28):16720–16724 (1996).
Enari et al., "Involvement of an ICE–like protease in Fas–mediated Apoptosis" *Nature* 375:78–81 (1995).
Franek and Chladkova–Sramkova, "Apoptosis and nutrition: Involvement of amino acid transport system in repression of hybridoma cell death" *Cytotechnology* 18:113–117 (1995).
Fraser and Evan, "A License to Kill" *Cell* 85:781–784 (1996).
Goswami et al., "Apoptosis in Batch Cultures of Chinese Hamster Ovary Cells" *Biotechnol. Bioeng.* 62:632–640 (1999).
Hsu et al., "TRADD–TRAF2 and TRADD–FADD interactions define two distinct TNF receptor 1 signal transduction pathways" *Cell* 84:299–308 (1996).
Itoh et al., "Overexpression of bcl–2, Apoptosis Suppressing Gene: Prolonged Viable Culture Period of Hybridoma and Enhanced Antibody Production" *Biotechnol. Bioeng.* 48:118–122 (1995).
Itoh et al., "The polypeptide encoded by the cDNA for human cell surface antigen Fas can mediate apoptosis" *Cell* 66:233–243 (1991).
Mastrangelo and Betenbaugh, "Overcoming apoptosis: new methods for improving protein–expression systems" *TIBTECH* 16:88–95 (1998).
Mercille and Massie, "Induction of Apoptosis in Nutrient–Deprived Cultures of Hybridoma and Myeloma Cells" *Biotechnol. Bioeng.* 44:1140–1154 (1994).

(List continued on next page.)

Primary Examiner—Gabrielle Bugaisky
(74) Attorney, Agent, or Firm—Diane L. Marschang

(57) ABSTRACT

The invention provided improved methods of making and producing recombinant proteins in in vitro cultures of host cells using apoptosis inhibitors. The use of one or more apoptosis inhibitors in the methods can reduce apoptosis in the cell cultures and markedly improve yield of the desired recombinant proteins.

21 Claims, 15 Drawing Sheets

OTHER PUBLICATIONS

Murray et al., "NSO Myeloma Cell Death: Influence of bcl–2 Overexpression" *Biotech. Bioeng.* 51:(3):298–304 (1996).

Muzio et al., "FLICE, A Novel FADD–Homologous ICE/CED–3–like Protease, Is Recruited to teh CD95 (Fas/APO–1) Death–Inducing Signaling Complex" *Cell* 85:817–827 (1996).

Nagata, S., "Apoptosis by Death Factor" *Cell* 88:355–365 (1997).

Pan et al., "Caspase–9, Bcl–$X_L$, and Apaf–1 Form a Ternary Complex" *Journal of Biological Chemistry* 273(10):5841–5845 (1998).

Presta et al., "Humanization of an Antibody Directed Against IgE" *J. Immunol.* 151(5):2623–2632 (Sep. 1, 1993).

Ray et al., "Viral Inhibition of Inflammation: Cowpox Virus Encodes an Inhibitor of the Interleukin–1β Converting Enzyme" *Cell* 69:597–604 (May 15, 1992).

Shak et al., "Recombinant Human DNase I Reduces the Viscosity of Cystic Fibrosis Sputum" *Proc. Natl. Acad. Sci. USA* 87(23):9188–9192 (Dec. 1990).

Simpson et al., "Prevention of Hybridoma Cell Death by bcl–2 During Suboptimal Culture Conditions" *Biotechnol. Bioeng.* 54:1–16 (1997).

Singh et al., "Cell Death in Bioreactors: A Role for Apoptosis" *Biotechnol. Bioeng.* 44:720–726 (1994).

Singh et al., "Enhancement of Survivability of Mammalian Cells by Overexpression of the Apoptosis–Suppressor Gene bcl–2" *Biotechnol. Bioeng.* 52:166–175 (1996).

Steller, H., "Mechanisms and Genes of Cellular Suicide" *Science* 267:1445–1449 (1995).

Suzuki et al., "Establishing apoptosis resistant cell lines for improving protein productivity of cell culture" *Cytotechnology* 23:55–59 (1997).

Tartaglia et al., "A novel domain within the 55 kd TNF receptor signals cell death" *Cell* 74(5):845–853 (1993).

Tewari and Dixit, "Fas– and Tumor Necrosis Factor–induced Apoptosis Is Inhibited by the Poxvirus crmA Gene Product" *Journal of Biological Chemistry* 270:3255–3260 (1995).

Tewari and Dixit, "Recent Advances in Tumor Necrosis Factor and CD40 Signaling" *Curr. Op. Genet. Develop.* 6:39–44 (1996).

Tewari et al., "Yama/CPP32β, a Mammalian Homolog of CED–3, Is a CrmA–Inhibitable Protease That Cleaves the Death Substrate Poly(ADP–Ribose) Polymerase" *Cell* 81:801–809 (1995).

van de Goor et al., "Inhibition of Apoptosis in Biofactors by "Anti–Apoptotic Genes"" *Cold Spring Harbor Meeting on Programmed Cell Death* (abstract only) pps. 228 (1999).

Verma et al., "Rel/NF–κB/IκB Family: Intimate Tales of Association and Dissociation" *Genes Develop.* 9:2723–2735 (1995).

Zanghi et al., "Serum Protects Protein–Free Competent Chinese Hamster Ovary Cells Against Apoptosis Induced by Nutrient Deprivation in Batch Culture" *Biotech. Bioeng.* 64:108–119 (1999).

Zou et al., "Apaf–1, a Human Protein Homologous to *C. elegans* CED–4, Participates in Cytochrome c–Dependent Activation of Caspase–3" *Cell* 90:405–413 (1997).

Database WPI Section Ch. Week 199735, Derwent Publications Ltd., London, GB; Class B04, AN 1997–380167 (Jun. 24, 1997).

Fujita et al., "Overexpression of bcl–2 Improved Survival of COS–1 Cells and Enhanced Transient Protein Production" *Journal of Fermentation and Bioengineering* 82(6):589–591 (1996).

Fujita et al., "Reinforcing apoptosis–resistance of COS and meyloma cells by transfecting with bcl–2 gene" *Cytotechnology* 25:25–33 (Feb. 1997).

Hedge et al., "Blk, a BH3–containing Mouse Protein That Interacts with Bcl–2 and Bcl–xL, Is a Potent Death Agonist" *The Journal of Biological Chemistry* 273(14):7783–7786 (Apr. 3, 1998).

Li et al., "Cytochrome c and dATP–Dependent Formation of Apaf–1/Caspase–9 Complex Initiates as Apoptotic Protease Cascade" *Cell* 91:479–489 (Nov. 14, 1997).

Mercille and Massie, "Apoptosis–Resistant E1B–19K–Expressing NS/0 Myeloma Cells Exhibit Increased Viability and Chimeric Antibody Productivity under Perfusion Culture Conditions" *Biotechnology and Bioengineering* 63(5):529–543 (Jun. 5, 1999).

Mercille et al., "Dose–Dependent Reduction of Apoptosis in Nutrient–Limited Cultures of NS/O Myeloma Cells Transfected with the E1B–19K Adenoviral Gene" *Biotechnology and Bioengineering* 63(5):516–528 ( A 1999).

Perkins et al., "Overexpression of Apaf–1 Promotes of Untreated and Paclitaxel– or Etoposide–treated HL–60 Cells" *Cancer Research* 58:4561–4566 (Oct. 15, 1998).

Seol and Billiar, "A Caspase–9 Variant Missing the Catalytic Site Is an Endogenous Inhibitor of Apoptosis" *The Journal of Biological Chemistry* 274(4):2072–2076 (Jan. 22, 1999).

Terada et al., "Improvement of Mammalian Cell Survival by Apoptosis–Inhibiting Genes and Caspase Inhibitors for Effective Use of Mammalian Cells" *Seibutsu–Kogaku Kaishi* 77(1):2–11 (Jan. 25, 1999).

tsang, "Mammalian Expression Vector with Two Multiple Cloning Sites for Expression of Two Foreign Genes" *Biotechniques* 22(1):68 (1997).

Zhou et al., "Fed–Batch Culture of Recombinant NSO Myeloma Cells with High Monoclonal Antibody Production" *Biotechnology of Bioengineering* 55(5):783–792 (Sep. 5, 1997).

pFLAG–CMV–2 Expression Vector, SIGMA Product Information.

Soo et al., "Overexpression of bcl–2 inhibits the apoptosis in rCHO" Abstracts of Papers American Chemical Society. 219th Meeting of The American Chemical Society, San Francisco, Mar. 26–30, 2000 219(1–2) (Abstract BIOT 245).

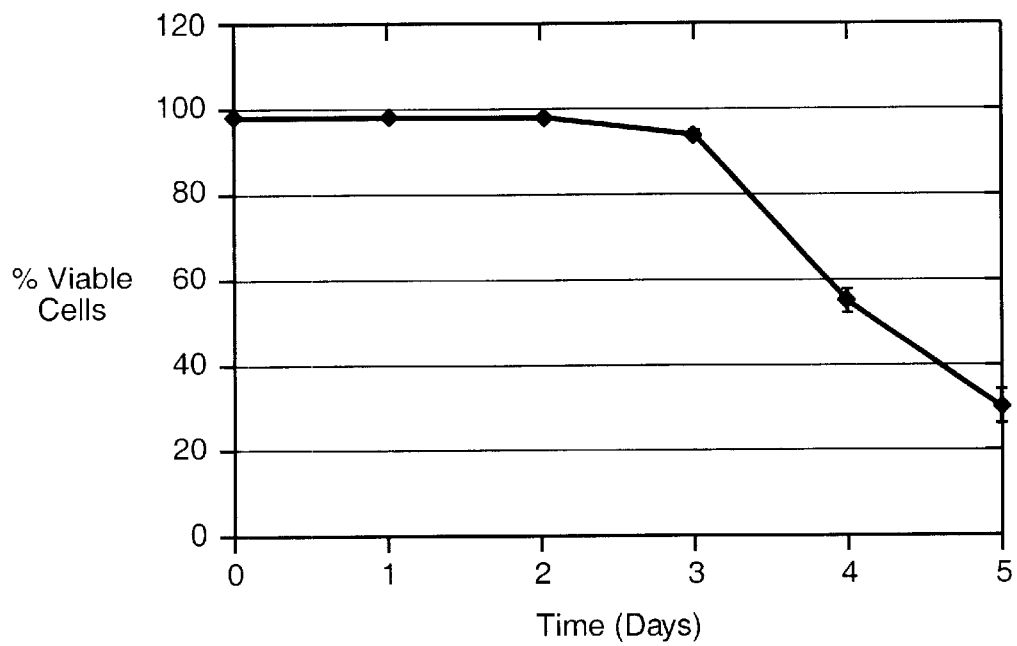
FIG._1A
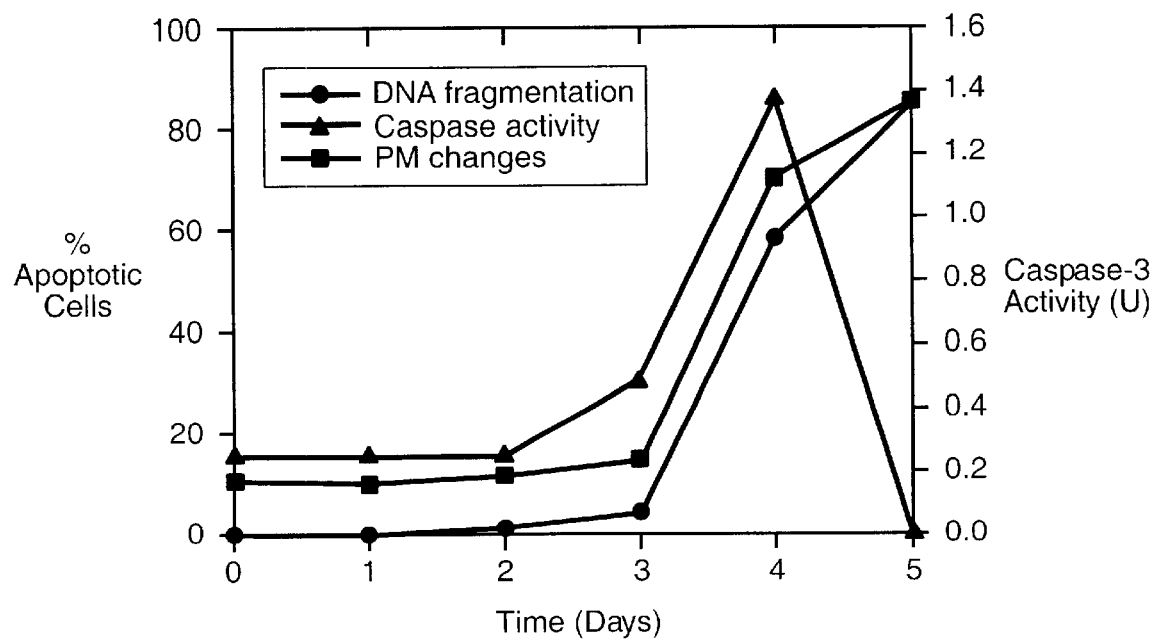
FIG._1B

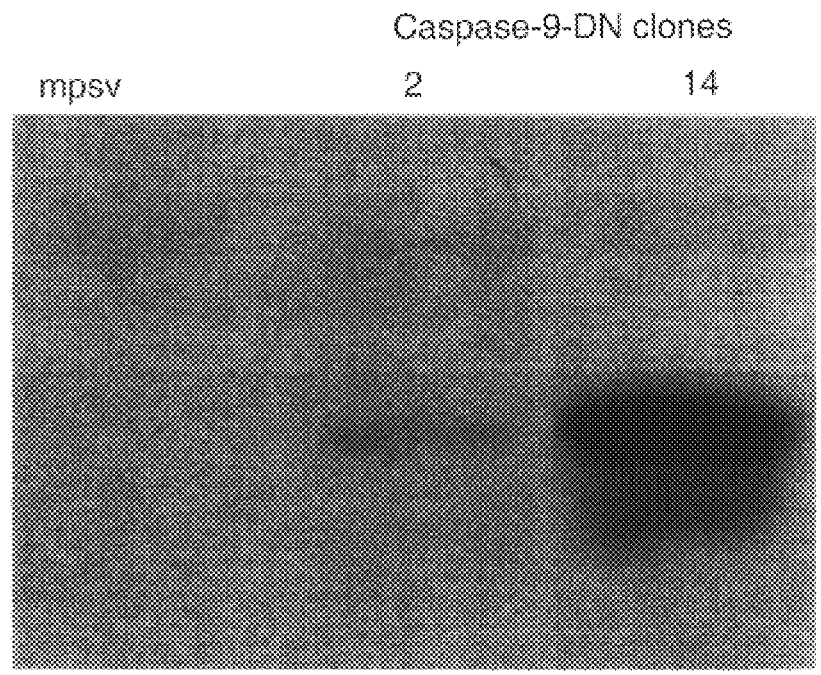
FIG._2
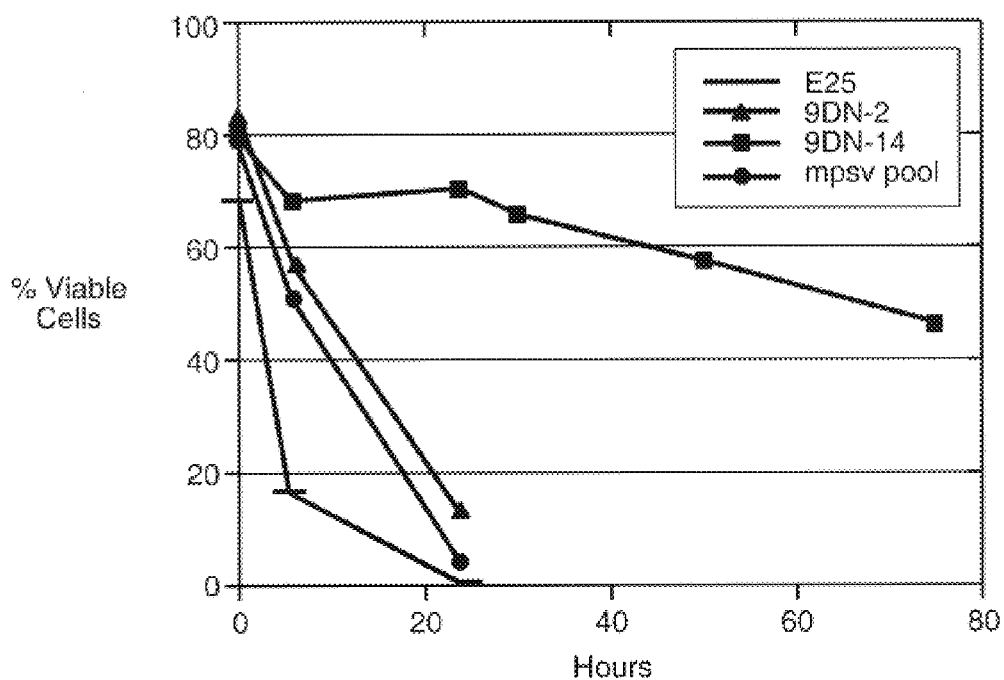
FIG._3

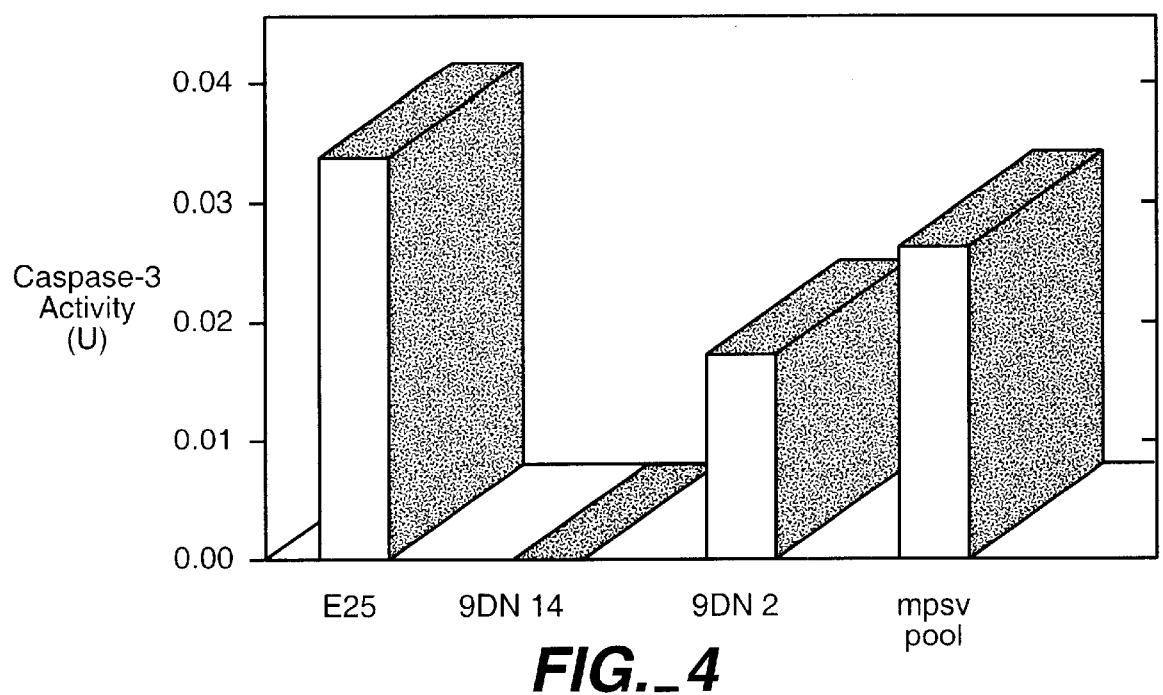
FIG._4
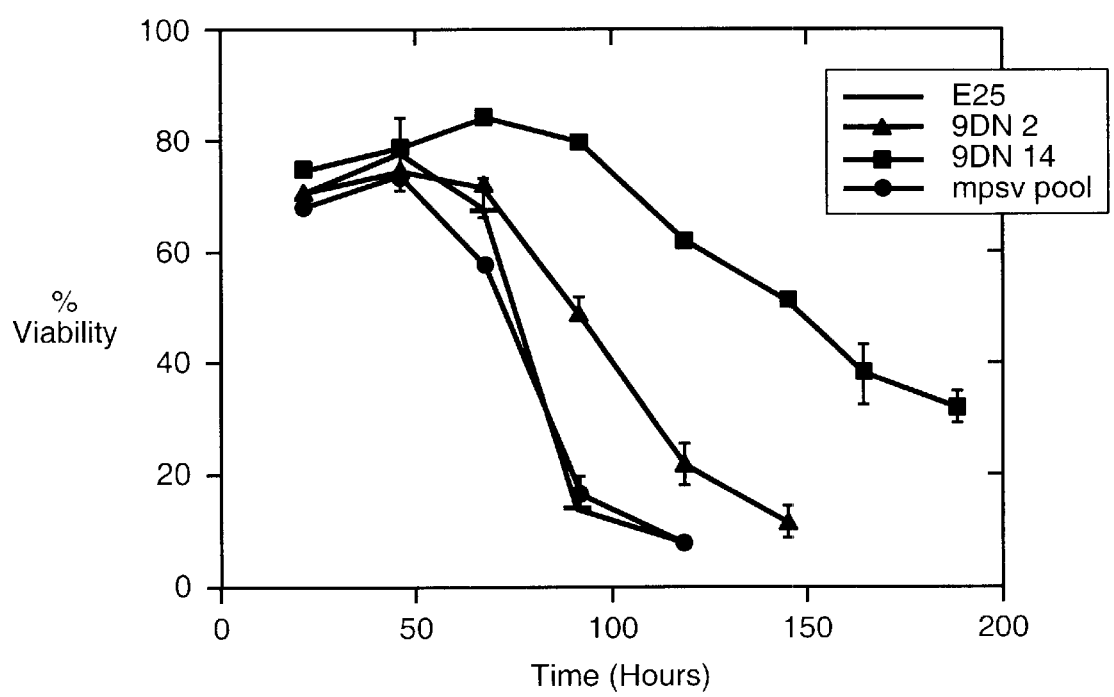
FIG._5

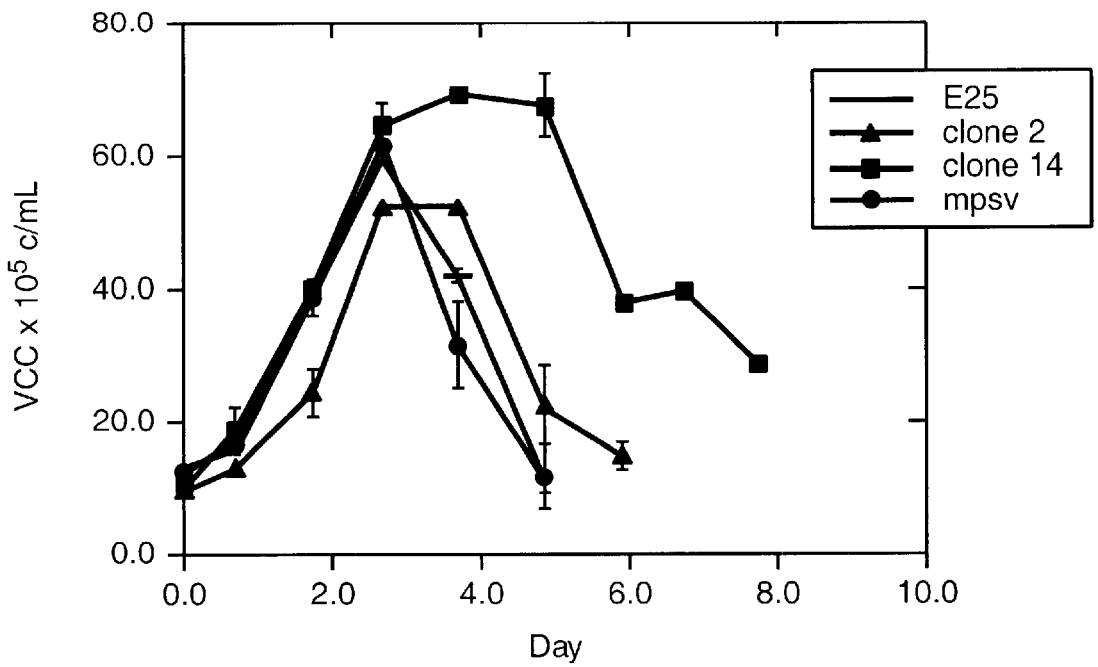
FIG._6
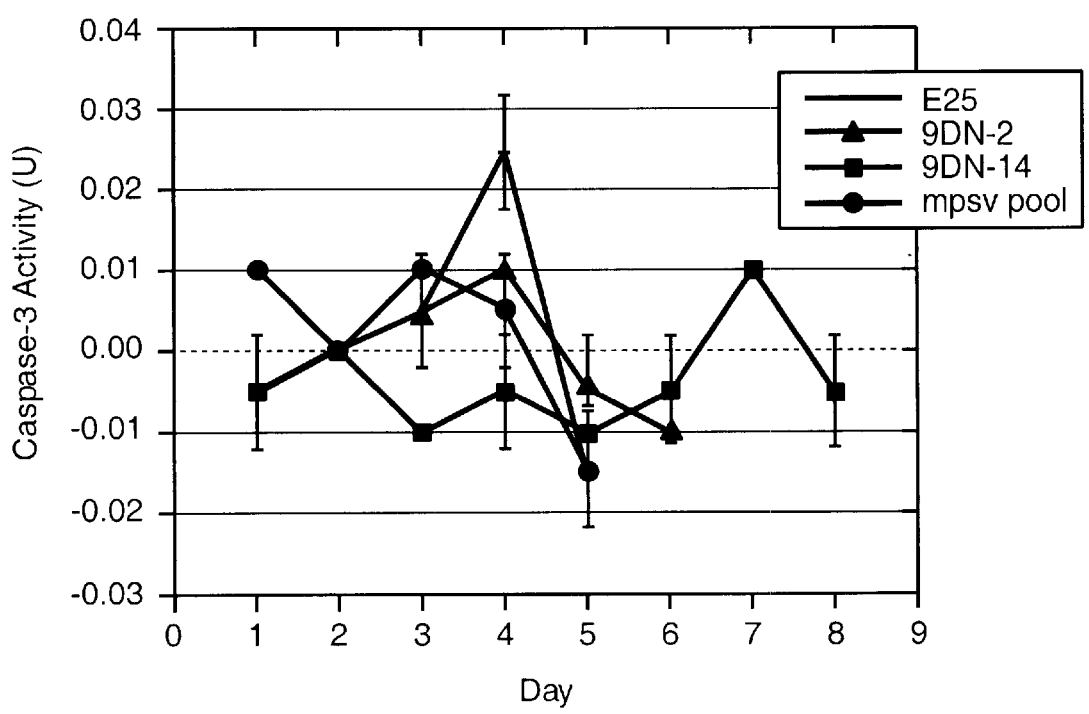
FIG._7

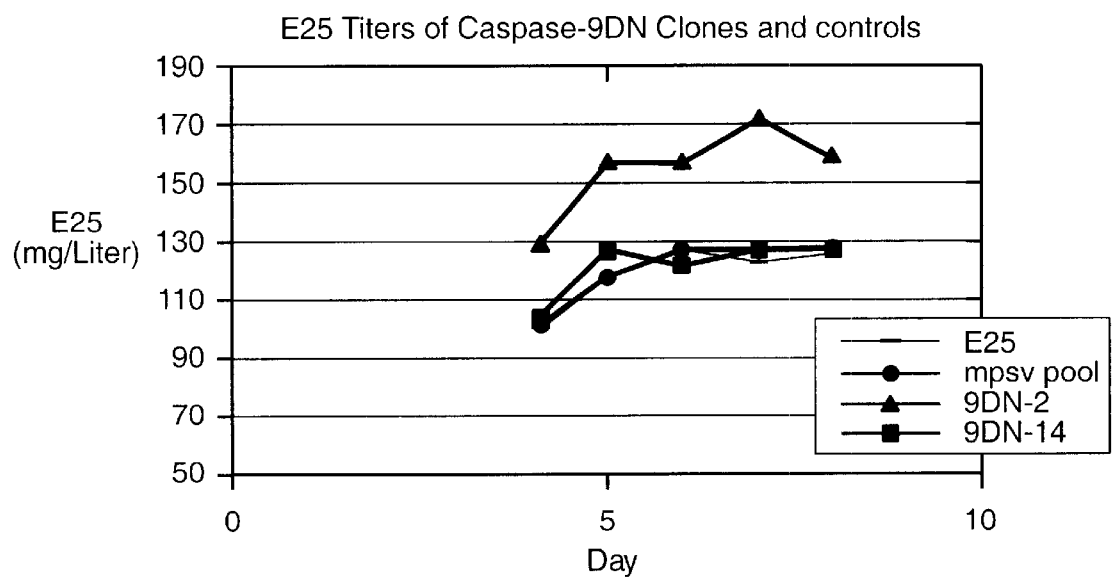
FIG._8
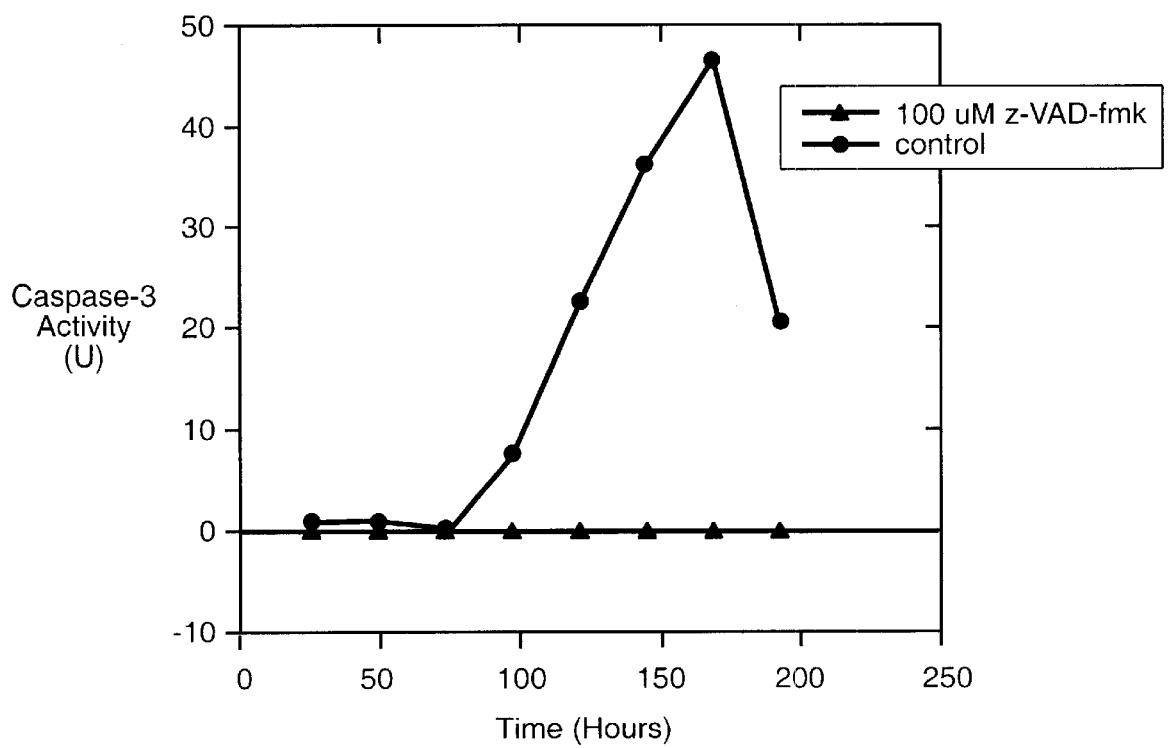
FIG._9

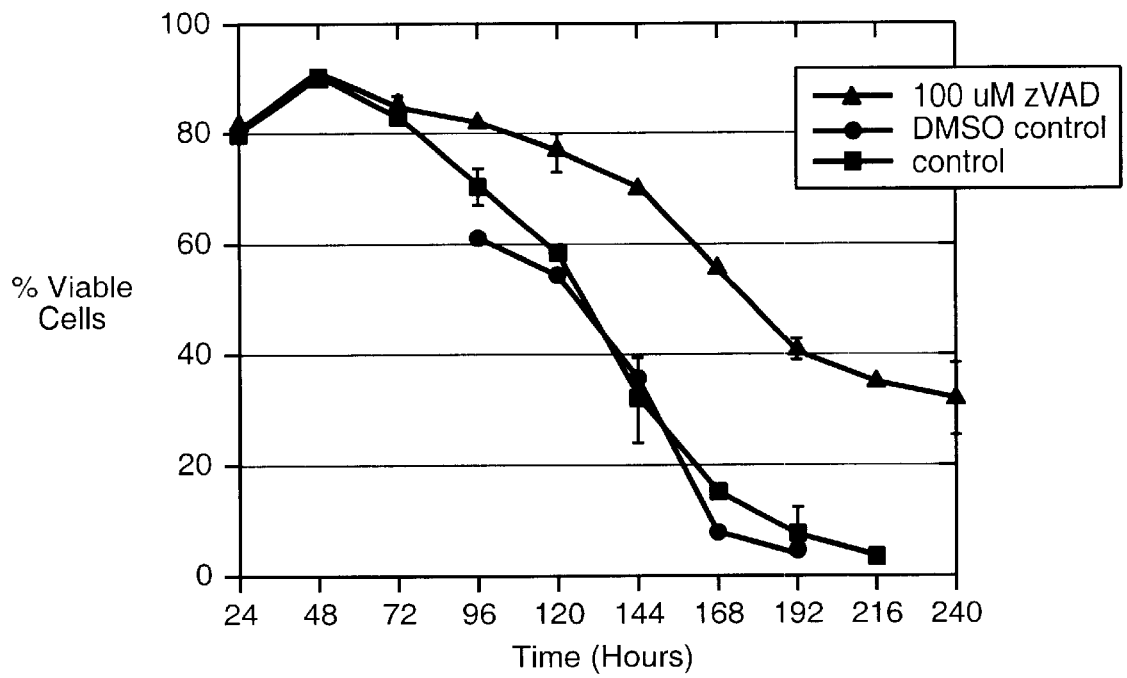
FIG._10
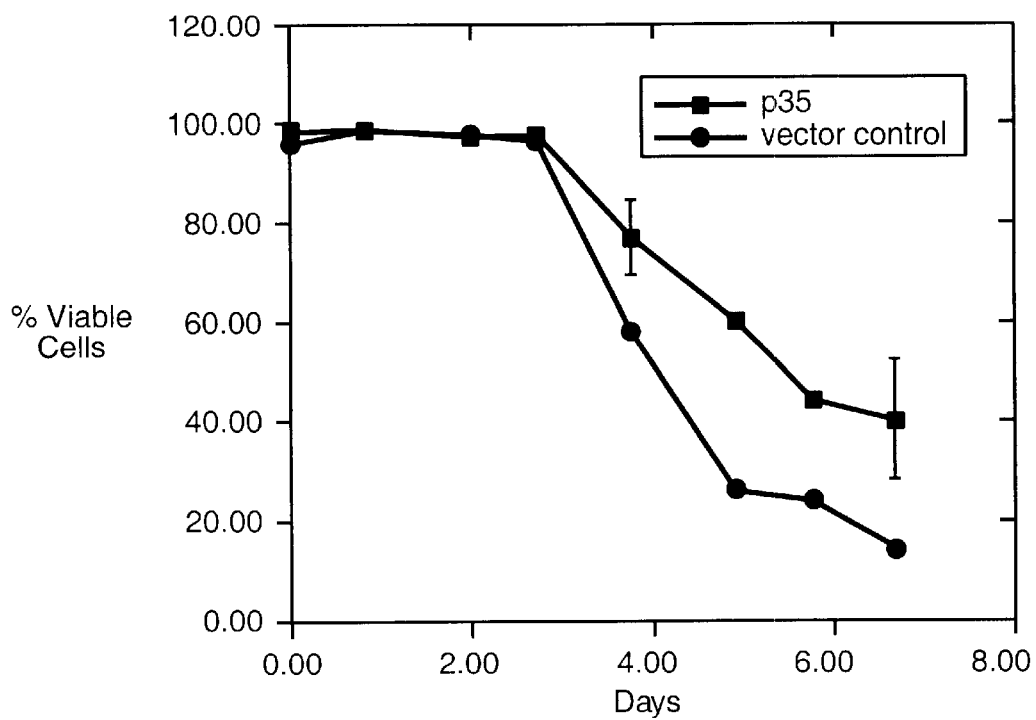
FIG._11

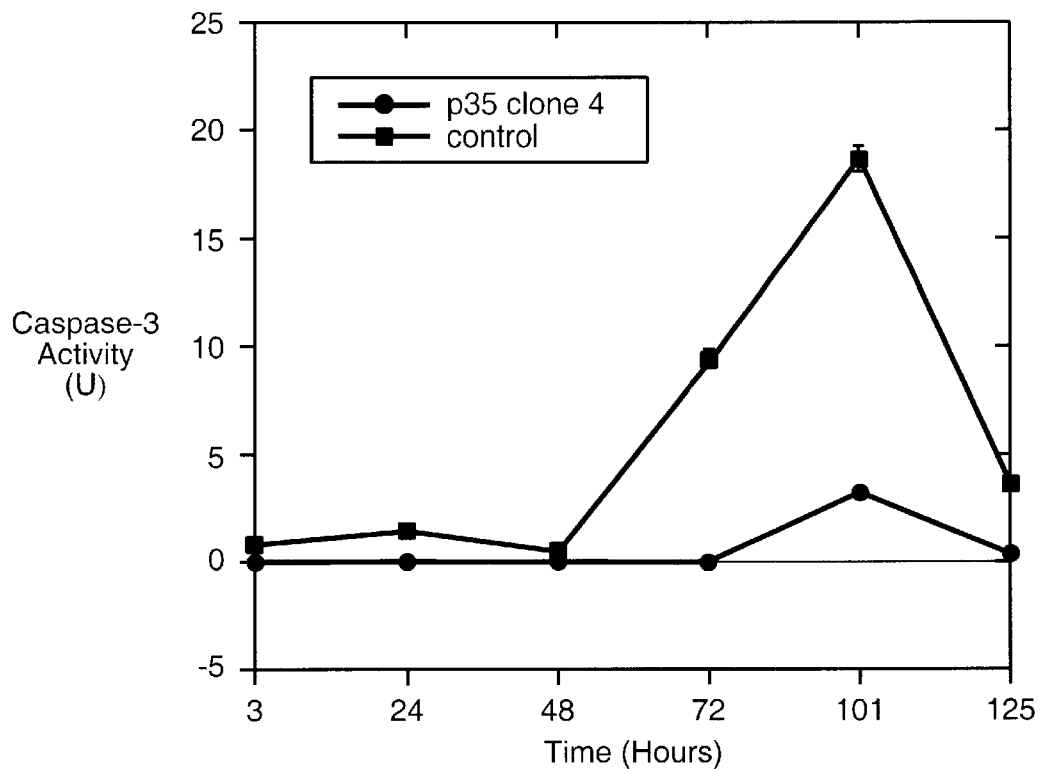
FIG._12
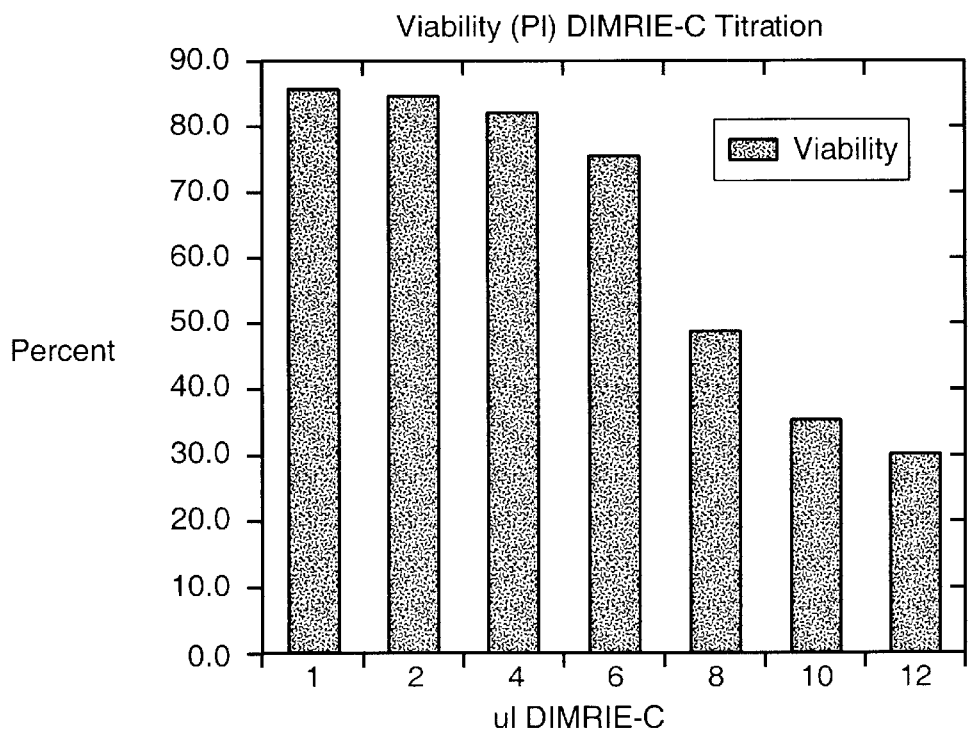
FIG._13

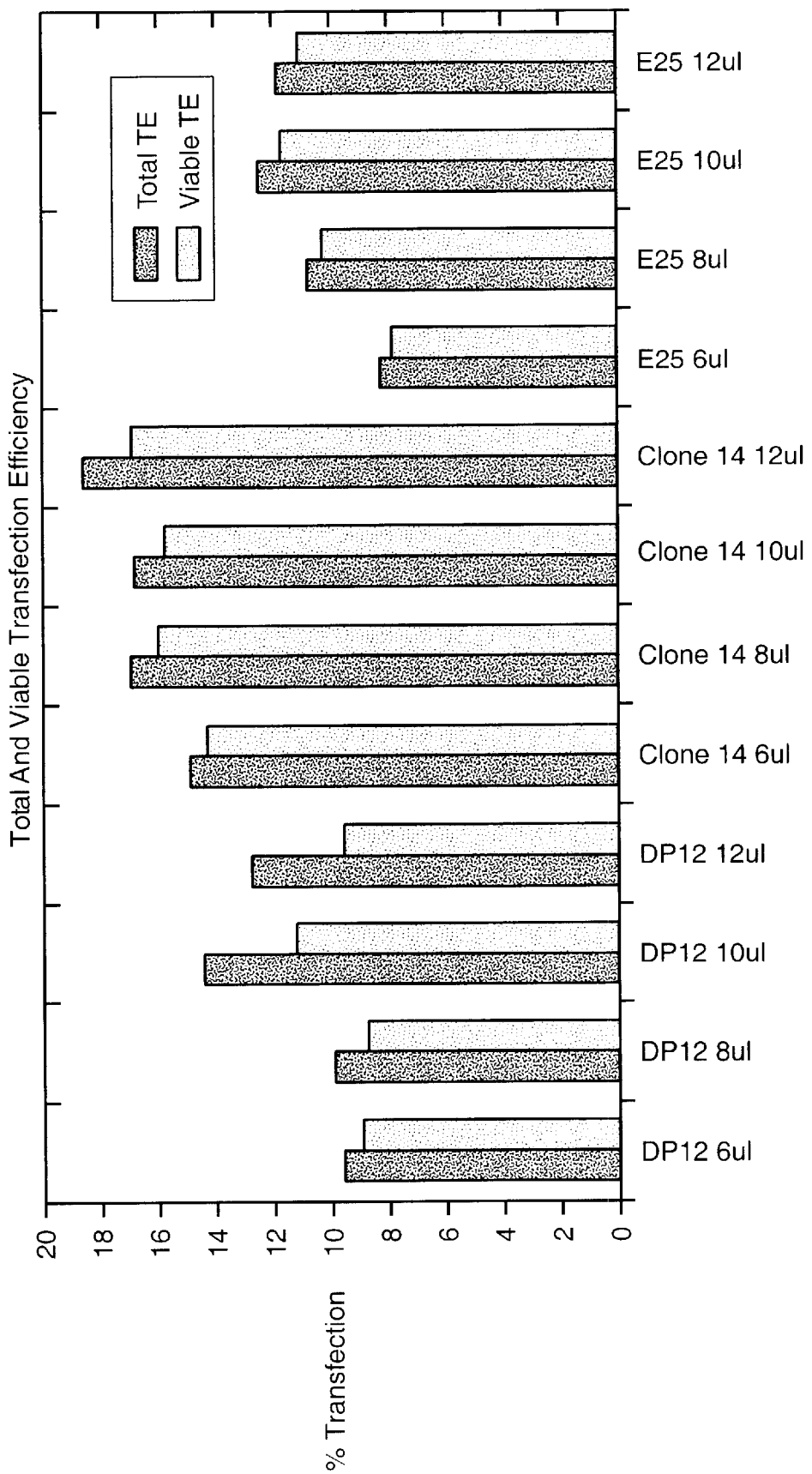
FIG._14

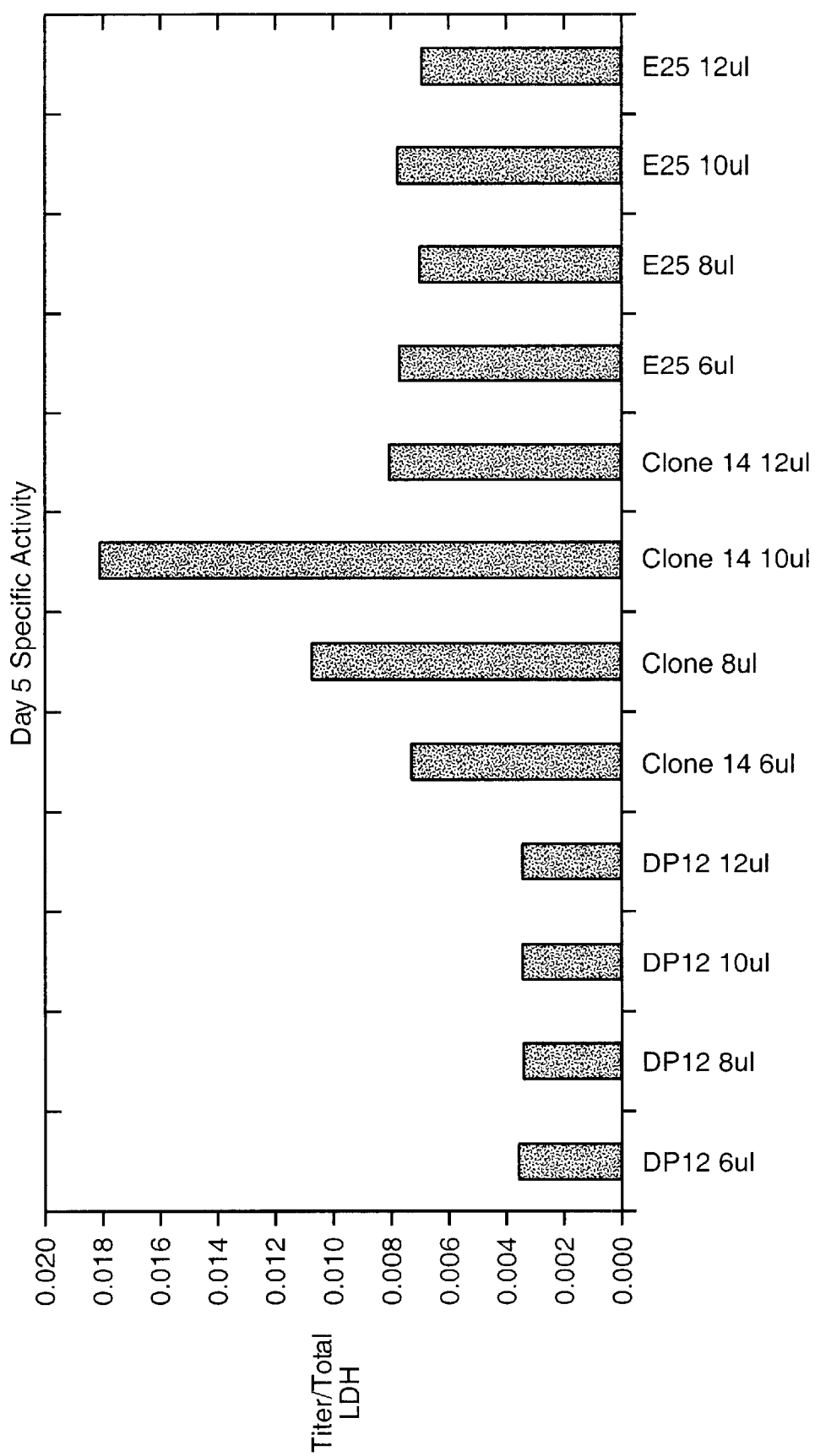
FIG._15

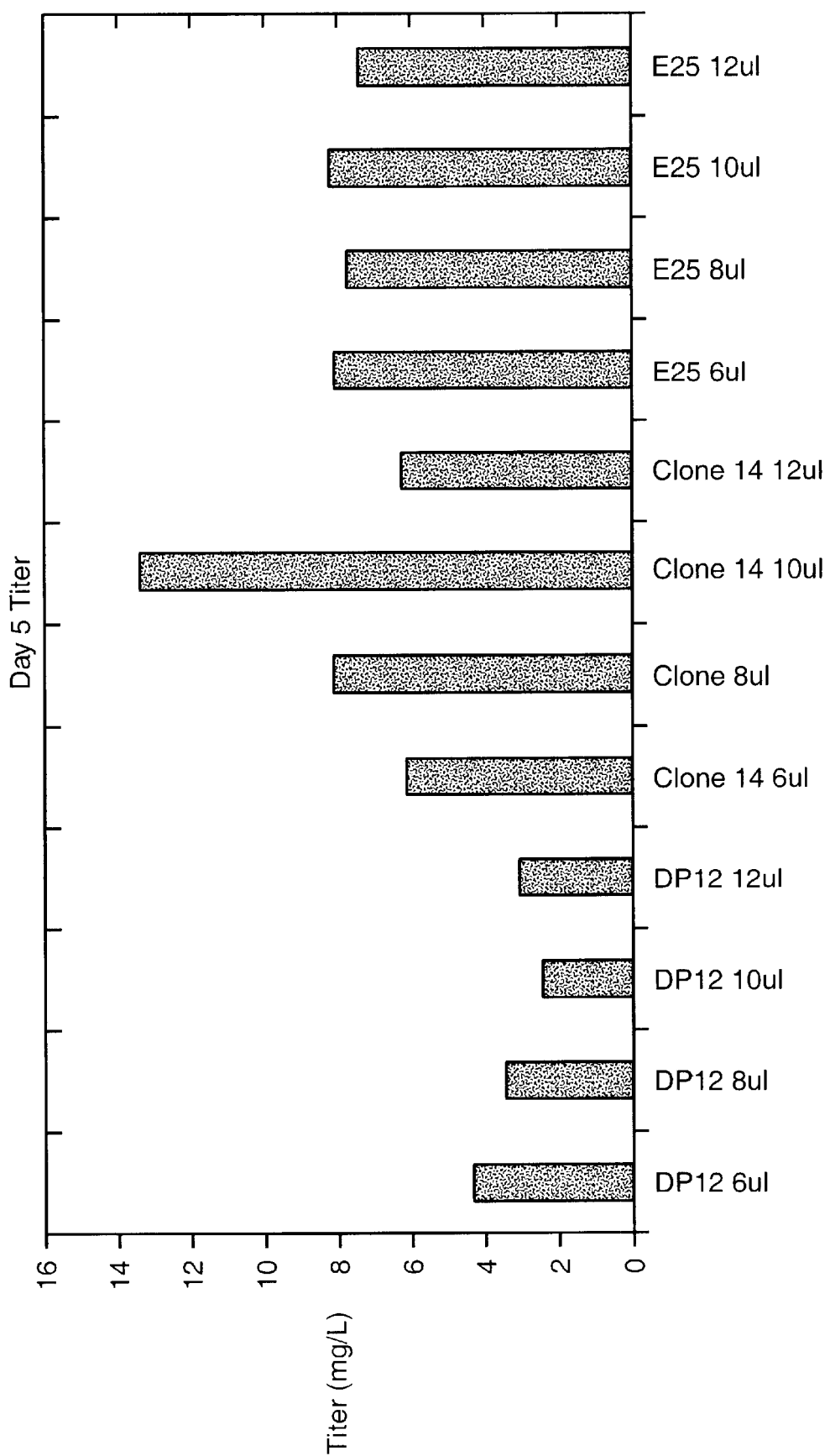

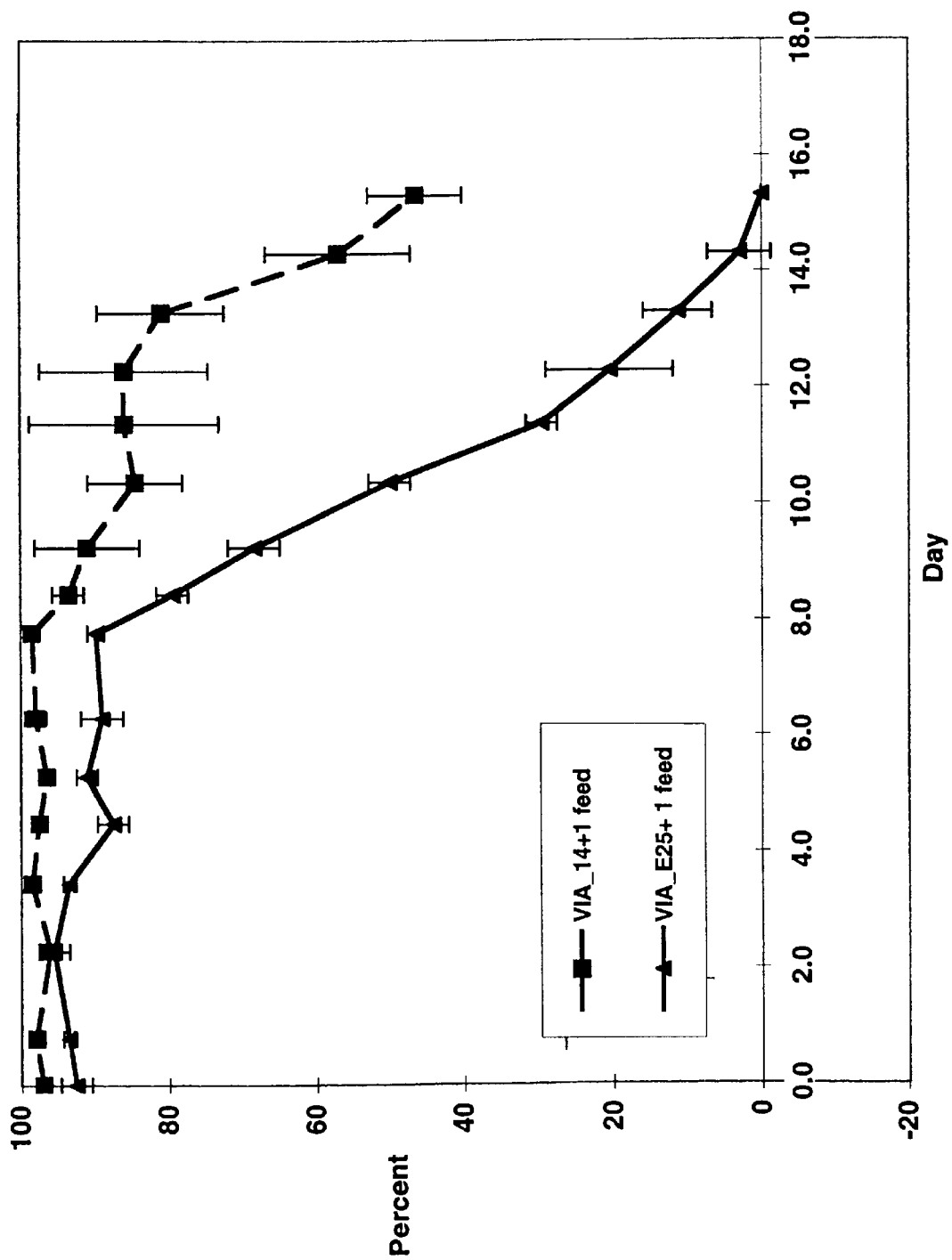
FIG._17

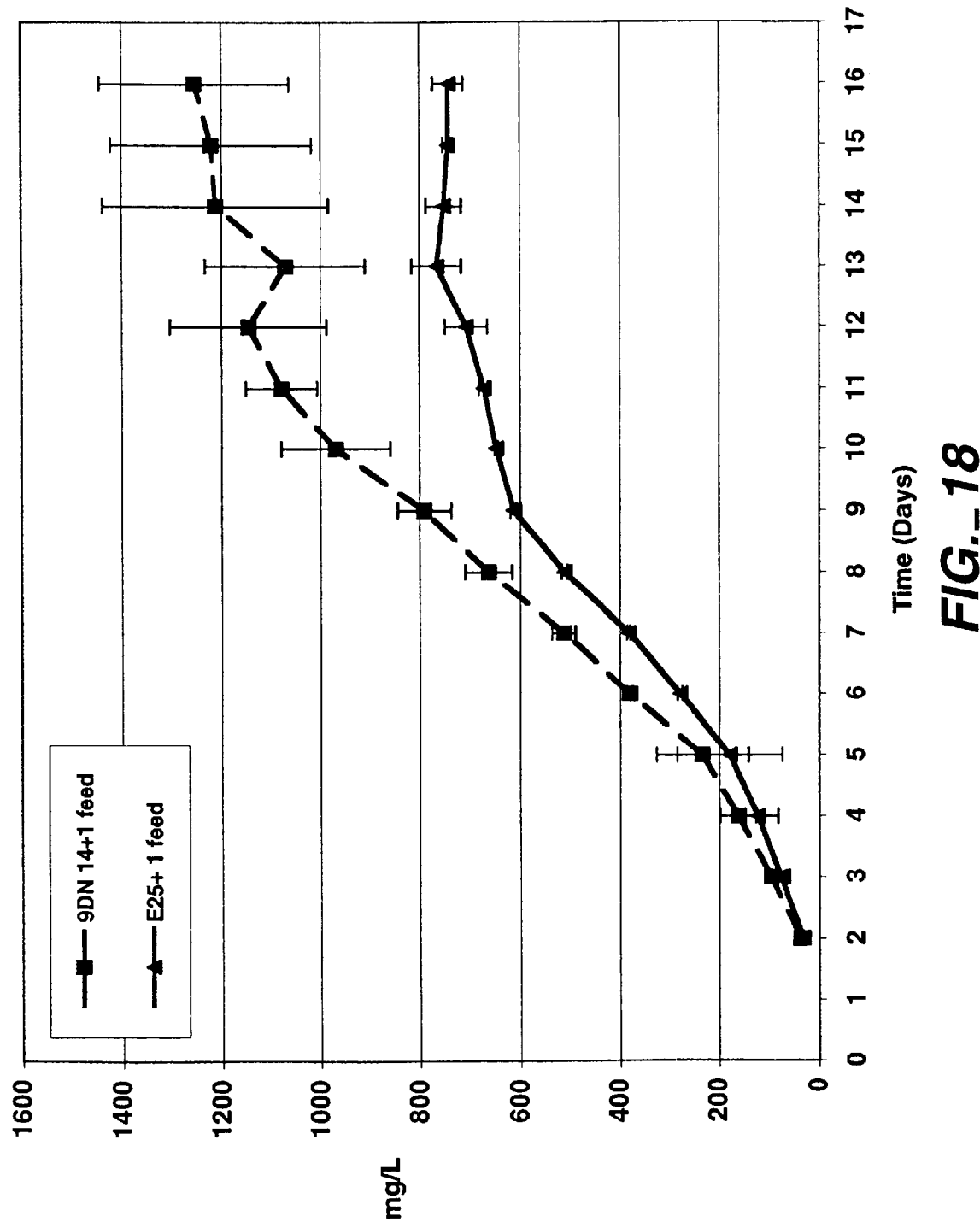
FIG._18

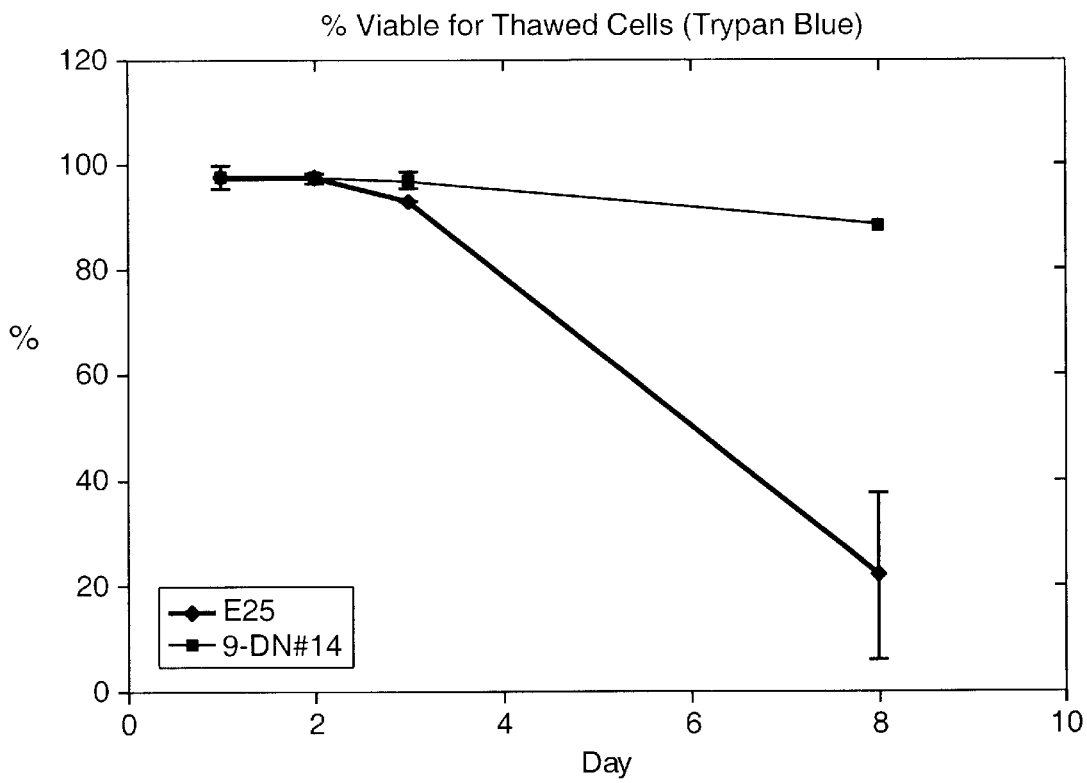
FIG._19
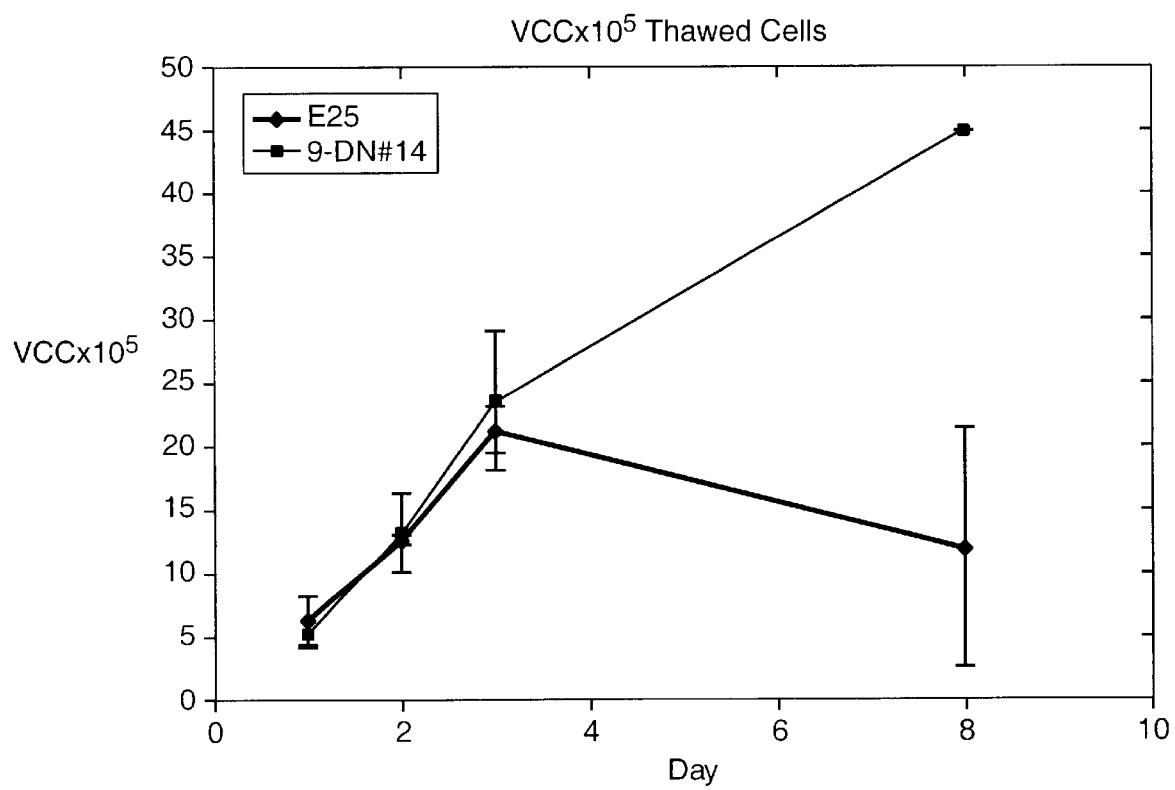
FIG._20

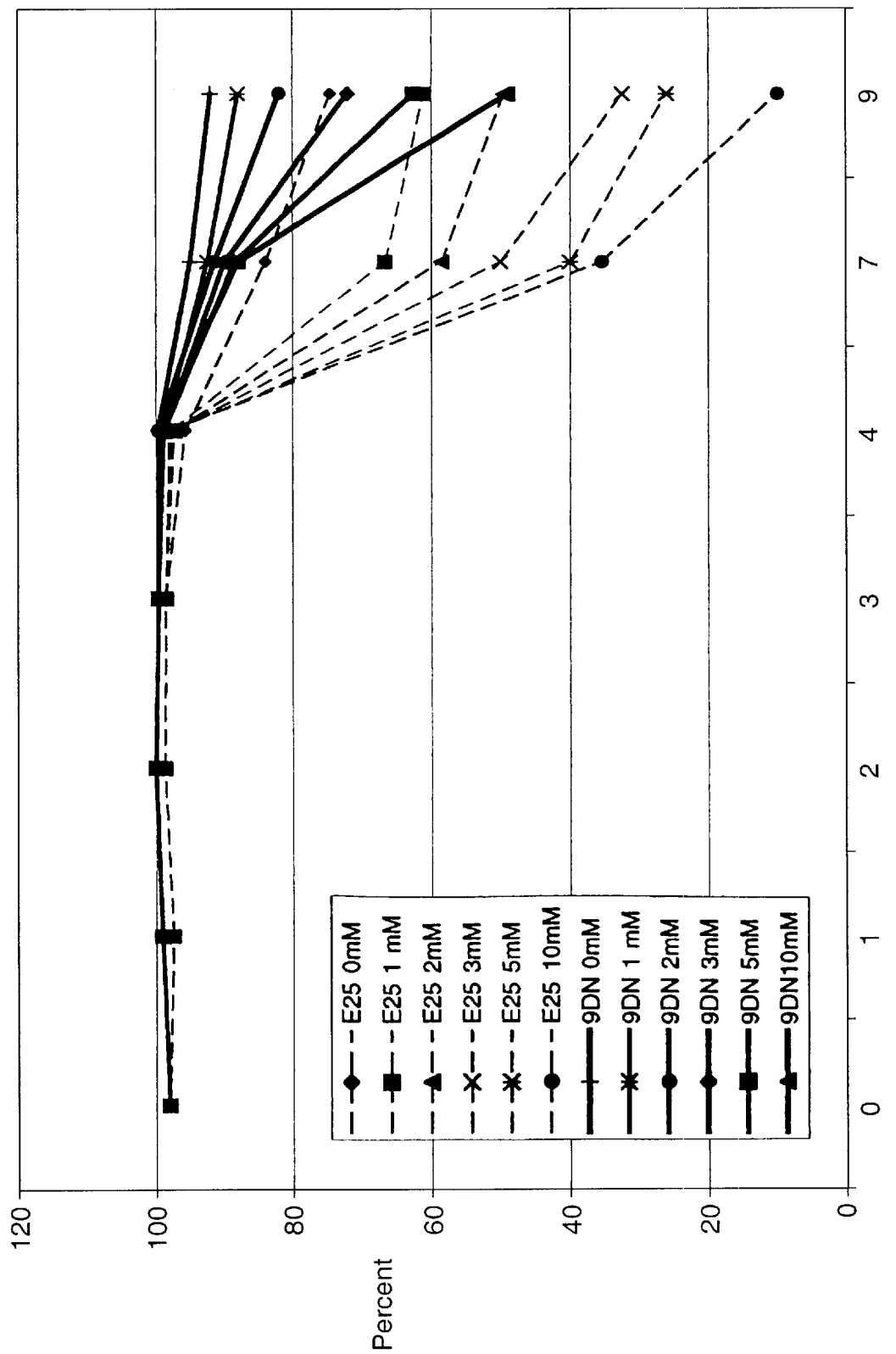
FIG._21

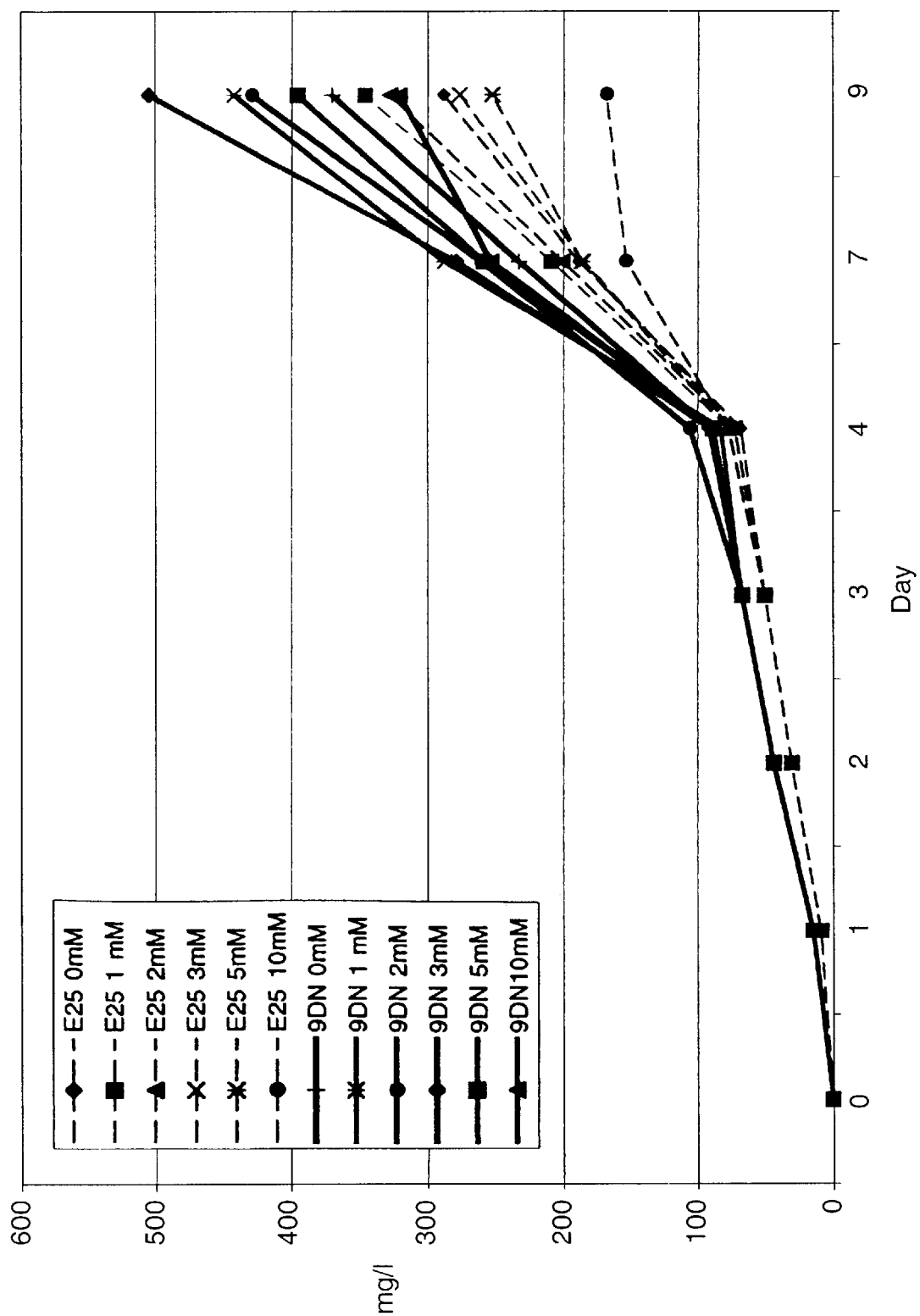
FIG._22

METHODS FOR MAKING RECOMBINANT PROTEINS USING APOPTOSIS INHIBITORS

RELATED APPLICATIONS

This is a non-provisional application claiming priority under Section 119(e) to provisional application no. 60/156,232, filed Sep. 27, 1999, the contents of which are incorporated herein by reference.

FIELD OF THE INVENTION

The present invention relates generally to improved methods of making recombinant proteins using one or more apoptosis inhibitors.

BACKGROUND OF THE INVENTION

Control of cell numbers in mammals is believed to be determined, in part, by a balance between cell proliferation and cell death. One form of cell death, sometimes referred to as necrotic cell death, is typically characterized as a pathologic form of cell death resulting from some trauma or cellular injury. In contrast, there is another, "physiologic" form of cell death which usually proceeds in an orderly or controlled manner. This orderly or controlled form of cell death is often referred to as "apoptosis" [see, e.g., Barr et al., Bio/Technology, 12:487–493 (1994); Steller et al., Science, 267:1445–1449 (1995)]. Apoptotic cell death naturally occurs in many physiological processes, including embryonic development and clonal selection in the immune system [Itoh et al., Cell, 66:233–243 (1991)].

Control of cell numbers in cell culture and bioreactors is also a balance between cell proliferation and cell death. There have been reports in the literature indicating cell death in bioreactors can be an apoptotic process [Suzuki E., et al., Cytotechnology, 23:55–59 (1997); Al-Rubeai, M. and Singh R. P, Curr. Opin. Biotech, 9:152–156 (1998)]. It has been described that the apoptotic process may be induced by nutrient deprivation [Franek F. and Chládkova-Šrámková K., Cytotechnology, 18:113–117 (1995); Mercille S. and Massie B., Biotechnol. Bioeng., 44:1140–1154 (1994); Singh R. P., et al., Biotechnol. Bioeng., 44:720–726 (1994)], serum deprivation [Singh R. P., et al., Biotechnol. Bioeng., 44:720–726 (1994); Zanghi A., et al., Biotech. Bioeng., 64:108–119 (1999)] or other controllable parameters of cell culture in bioreactors, but is not controlled fully because of bioreactor mechanics, a lack of full understanding of necessary culture parameters, or other undetermined causes.

As presently understood, the apoptosis or cell death program contains at least three important elements— activators, inhibitors, and effectors; in C. elegans, these elements are encoded respectively by three genes, Ced-4 4, Ced-9 and Ced-3 [Steller, Science, 267:1445 (1995); Chinnaiyan et al., Science, 275:1122–1126 (1997); Wang et al., Cell, 90:1–20 (1997)]. Two of the TNFR family members, TNFR1 and Fas/Apo1 (CD95), can activate apoptotic cell death [Chinnaiyan and Dixit, Current Biology, 6:555–62 (1996); Fraser and Evan, Cell; 85:781–784 (1996)]. TNFR1 is also known to mediate activation of the transcription factor, NF-KB [Tartaglia et al., Cell, 74:845–853 (1993); Hsu et al., Cell, 84:299–308 (1996)]. In addition to some ECD homology, these two receptors share homology in their intracellular domain (ICD) in an oligomerization interface known as the death domain [Tartaglia et al., supra; Nagata, Cell, 88:355 (1997)]. Death domains are also found in several metazoan proteins that regulate apoptosis, namely, the Drosophila protein, Reaper, and the mammalian proteins referred to as FADD/MORT1, TRADD, and RIP [Cleaveland and Ihle, Cell, 81:479–482 (1995)].

Upon ligand binding and receptor clustering, TNFR1 and CD95 are believed to recruit FADD into a death-inducing signaling complex. CD95 purportedly binds FADD directly, while TNFR1 binds FADD indirectly via TRADD [Chinnaiyan et al., Cell, 81:505–512 (1995); Boldin et al., J. Biol. Chem., 270:387–391 (1995); Hsu et al., supra; Chinnaiyan et al., J. Biol. Chem., 271:4961–4965 (1996)]. It has been reported that FADD serves as an adaptor protein which recruits the Ced-3-related protease, MACH-alpha/FLICE (caspase 8), into the death signaling complex [Boldin et al., Cell, 85:803–815 (1996); Muzio et al., Cell, 85:817–827 (1996)]. MACH-alpha/FLICE appears to be the trigger that sets off a cascade of apoptotic proteases, including the interleukin-1beta converting enzyme (ICE) and CPP32/Yama, which may execute some critical aspects of the cell death programme [Fraser and Evan, supra].

It was recently disclosed that programmed cell death involves the activity of members of a family of cysteine proteases related to the C. elegans cell death gene, ced-3, and to the mammalian IL-1-converting enzyme, ICE. The activity of the ICE and CPP32/Yama proteases can be inhibited by the product of the cowpox virus gene, crmA [Ray et al., Cell, 69:597–604 (1992); Tewari et al., Cell, 81:801–809 (1995)]. Recent studies show that CrmA can inhibit TNFR1- and CD95-induced cell death [Enari et al., Nature, 375:78–81 (1995); Tewari et al., J. Biol. Chem., 270:3255–3260 (1995)].

As reviewed recently by Tewari et al., TNFR1, TNFR2 and CD40 modulate the expression of proinflammatory and costimulatory cytokines, cytokine receptors, and cell adhesion molecules through activation of the transcription factor, NF-KB [Tewari et al., Curr. Op. Genet. Develop., 6:39–44 (1996)]. NF-KB is the prototype of a family of dimeric transcription factors whose subunits contain conserved Rel regions [Verma et al., Genes Develop., 9:2723–2735 (1996); Baldwin, Ann. Rev. Immunol., 14:649–681 (1996)]. In its latent form, NF-KB is complexed with members of the IKB inhibitor family; upon inactivation of the IKB in response to certain stimuli, released NF-KB translocates to the nucleus where it binds to specific DNA sequences and activates gene transcription.

For recent reviews of such signaling pathways, see, e.g., Ashkenazi et al., Science, 281:1305–1308 (1998); Nagata, Cell, 88:355–365 (1997).

To date, there have been conflicting reports as to the effects of caspase inhibitors and expression of anti-apoptotic genes on cultured recombinant cells. For instance, Murray et al., Biotech. Bioeng., 51:298–304 (1996) describe that overexpression of bcl-2 in NSO myeloma cells failed to affect the decline phase characteristics of the cultured cells. Other investigators have found, in contrast, that bcl-2 can be effective in preventing different cell lines from death under cell-culture conditions [see, e.g., Itoh et al., Biotechnol. Bioeng., 48:118–122 (1995); Mastrangelo et al., TIBTECH, 16:88–95 (1998); Simpson et al., Biotechnol. Bioeng., 54:1–16 (1997); Singh et al., Biotechnol. Bioeng., 52:166–175 (1996)]. Goswami et al., Biotechnol. Bioeng., 62:632–640 (1999) report that they found that the caspase inhibitor, z-VAD-fmk, was unable to substantially extend the life of a serum-free culture of CHO cells.

SUMMARY OF THE INVENTION

The present invention is based on Applicants' findings that employing one or more apoptosis inhibitor(s) in recombinant cell culturing and protein production can markedly reduce apoptosis in the cell culture and improve recombinant protein production techniques. The methods disclosed in present application are useful, for example, in prolonging cell viability in cell cultures or improving or enhancing yield of the recombinant proteins from the cell cultures. Further improvements provided by the invention are described in detail below.

In one embodiment, the invention provides a method of making recombinant proteins using one or more apoptosis inhibitors. The method includes the steps of (a) providing a vector comprising a gene encoding an apoptosis inhibitor, (b) providing a vector comprising a gene encoding a protein of interest, (c) providing a host cell, (d) transforming or transfecting the host cell with the vectors referred to in steps (a) and (b), (e) providing cell culture media, (f) culturing the transformed or transfected host cell(s) in the culture media under conditions sufficient to express the protein of interest and the apoptosis inhibitor, and (g) recovering or purifying the protein of interest from the host cells and/or the cell culture media. Optionally, the method further includes the step of admixing an additional apoptosis inhibitor into the culture media. In the method, the respective genes encoding the apoptosis inhibitor and the protein of interest may be inserted into a single vector (e.g., co-transfected in a single vector), or alternatively, be inserted into two separate vectors. Preferably, the respective genes encoding the apoptosis inhibitor and the protein of interest are inserted into two separate vectors, each vector having a different type of selection marker from the other vector. Optionally, the method provides for transient expression of the protein of interest and stable or transient expression of the apoptosis inhibitor. Optionally, the gene encoding the apoptosis inhibitor comprises a gene encoding the caspase-9-DN protein or baculovirus p35.

In another embodiment, the method includes the steps of (a) providing a vector comprising a gene encoding a protein of interest, (b) providing a host cell comprising DNA encoding an apoptosis inhibitor, (c) transforming or transfecting the host cell(s) with the vector referred to in step (a), (d) providing cell culture media, (e) culturing the transformed or transfected host cell(s) in the culture media under conditions sufficient to express the protein of interest and the apoptosis inhibitor, and (f) recovering or purifying the protein of interest from the host cells and/or cell culture media. Optionally, the gene encoding the apoptosis inhibitor may be stably integrated into the genome of the host cell. Optionally, the method includes the further step of admixing an additional apoptosis inhibitor molecule into the culture media. Optionally, the method provides for transient expression of the protein of interest and stable or transient expression of the apoptosis inhibitor.

In another embodiment, the method includes the steps of (a) providing a vector comprising a gene encoding a protein of interest, (b) providing a host cell, (c) transforming or transfecting the host cell with the vector referred to in step (a), (d) providing cell culture media, (e) providing an apoptosis inhibitor, (f) admixing the apoptosis inhibitor into the culture media, (g) culturing the host cell(s) in the culture media under conditions sufficient to express the protein of interest, and (h) recovering or purifying the protein of interest from the host cells and/or the cell culture media. Optionally, the method provides for transient expression of the protein of interest.

In another embodiment, the method includes the steps of (a) providing a vector comprising a gene encoding an apoptosis inhibitor, (b) providing a vector comprising a gene encoding a protein of interest, (c) providing a host cell, (d) transforming or transfecting the host cell with the vectors referred to in steps (a) and (b), (e) providing cell culture media, (f) culturing the transformed or transfected host cell(s) in the culture media under conditions sufficient to express the protein of interest and the apoptosis inhibitor, and (g) freezing and subsequently thawing the host cells and/or the cell culture media. Optionally, the method further includes the step of admixing an additional apoptosis inhibitor into the culture media in steps (e) or (f). In the method, the respective genes encoding the apoptosis inhibitor and the protein of interest may be inserted into a single vector, or alternatively, be inserted into two separate vectors. Preferably, the respective genes encoding the apoptosis inhibitor and the protein of interest are inserted into two separate vectors, each vector having a different type of selection marker from the other vector. Optionally, the method provides for transient expression of the protein of interest and stable or transient expression of the apoptosis inhibitor.

In another embodiment, the method includes the steps of (a) providing a vector comprising a gene encoding a protein of interest, (b) providing a host cell comprising DNA encoding an apoptosis inhibitor, (c) transforming or transfecting the host cell(s) with the vector referred to in step (a), (d) providing cell culture media, (e) culturing the transformed or transfected host cell(s) in the culture media under conditions sufficient to express the protein of interest and the apoptosis inhibitor, and (f) freezing and subsequently thawing the host cells and/or cell culture media. Optionally, the gene encoding the apoptosis inhibitor may be stably integrated into the genome of the host cell. Optionally, the method includes the further step of admixing an additional apoptosis inhibitor molecule into the culture media. Optionally, the method provides for transient expression of the protein of interest and stable or transient expression of the apoptosis inhibitor.

In another embodiment, the method includes the steps of (a) providing a vector comprising a gene encoding a protein of interest, (b) providing a host cell, (c) transforming or transfecting the host cell with the vector referred to in step (a), (d) providing cell culture media, (e) providing an apoptosis inhibitor, (f) admixing the apoptosis inhibitor into the culture media, (g) culturing the host cell(s) in the culture media under conditions sufficient to express the protein of interest, and (h) freezing and subsequently thawing the host cells and/or the cell culture media. Optionally, the method provides for transient expression of the protein of interest.

In a still further embodiment, the invention provides for improved transfection methods wherein use of one or more apoptosis inhibitor(s) and increased concentrations of transfection reagent can be employed to increase transfection efficiency.

In an even further embodiment, the invention provides a protein of interest produced in accordance with any of the methods described herein. The protein of interest may comprise a mammalian protein or non-mammalian protein, and may optionally comprise a receptor or a ligand. In one embodiment of the invention, the protein of interest will comprise a protein which itself is capable of inducing apoptosis in mammalian or non-mammalian cells in vitro or in vivo, such as Apo-2 ligand/TRAIL, Fas ligand, or TNF-alpha.

BRIEF DESCRIPTION OF THE DRAWINGS

FIG. 1A shows a graph illustrating cell viability of CHO cells grown in a 2 liter bioreactor. The data show that the cells grown in bioreactors may begin to lose viability as early as day 3, often followed by a dramatic drop in viability on the following day(s).

FIG. 1B shows a graph illustrating the results of three apoptosis assays performed on the CHO cells (referred to in FIG. 1A and Example 1): caspase-3 activation, DNA fragmentation and annexin/PI binding (plasma membrane ("PM") changes). Activation of caspases was first detected on day 3, the day that drop in viability was detected (FIG. 1A).

FIG. 2 shows a Western blot analysis of lysates from caspase-9-DN transfected clones. A clone transfected with a mpsv vector (alone) was used as a control. The blot was probed with rabbit anti-caspase-9 antiserum (Pharmingen) and developed using chemiluminescence.

FIG. 3 shows the results of an assay wherein caspase-9-DN clones 2 and 14, as well as controls (E25 untransfected cells and mpsv vector transfected cells) were incubated with an apoptosis inducer, staurosporine (1 micromolar). Samples were taken and cells were analyzed for the % of viable cells.

FIG. 4 shows an analysis of caspase-3 activity or cell samples taken at 24 hours post-induction with 1 micromolar staurosporine.

FIGS. 5–8 show assay results of caspase-9-DN expressing clones 2 and 14, as well as controls, scaled up and seeded at 1 million cells/ml in a 2 liter bioreactor. Samples were taken daily and were analyzed for viability (FIG. 5), viable cell count (FIG. 6), activity of caspase-3 (FIG. 7) and the concentration of the protein of interest (E25 antibody) secreted into the medium (FIG. 8).

FIGS. 9–10 show assay results of CHO cells seeded in 60 mm dishes and exposed to caspase inhibitor, z-VAD-fmk (added to the cell culture at 100 micromolar concentration, 48 hours after seeding). The z-VAD-fmk inhibitor was added to the culture every 24 hours thereafter. Samples were taken every day and analyzed for caspase-3 activity (FIG. 9) and the % viable cells (FIG. 10).

FIGS. 11–12 show assay results of a Baculovirus p35 expressing clone grown in a 2 liter bioreactor and assayed daily for cell viability (FIG. 11) and caspase-3 activity (FIG. 12). The control is a clone transfected with a vector, cpc.

FIG. 13 shows a bar diagram of the effects of various concentrations of the transfection reagent, DMRIE-C, on cell viability.

FIG. 14 shows a comparison of total and viable transfection efficiencies obtained for caspase-9-DN clone 14 and controls, CHO DP12 cells and E25 antibody expressing CHO DP12 cells.

FIG. 15 shows a comparison of the specific productivity (as measured in Dnase titer/total LDH) obtained for caspase-9-DN clone 14 and controls, CHO DP12 cells and E25 antibody expressing CHO DP12 cells.

FIG. 16 shows a comparison of the DNase titer obtained for caspase-9-DN clone 14 and controls, CHO DP12 cells and E25 antibody expressing CHO DP12 cells.

FIGS. 17 and 18 show viability and titers of caspase-9-DN and E25 control grown in 2 liter bioreactors with temperature shift, concentrated medium and a feed.

FIGS. 19 and 20 show viability and viable cell count of cultures of E25 control and caspase-9-DN clone 14 seeded into spinners from frozen vials. Data were obtained by trypan blue exclusion.

FIGS. 21 and 22 show viability and E25 titers of cultures of E25 control cells and caspase-9-DN clone 14 upon induction of expression by butyrate.

DETAILED DESCRIPTION OF THE PREFERRED EMBODIMENTS

I. Definitions

The term "apoptosis inhibitor" is used herein to refer to a molecule or substance whose expression or presence in an in vitro cell culture provides a reduction or inhibition of apoptosis in the cultured cells, or provides resistance of the cultured cells to apoptotic stimuli. The apoptosis inhibitor may comprise a protein or protein-like molecule, or an organic or inorganic molecule. The apoptosis inhibitor may be present (and/or function) intracellularly, extracellularly, or at the cell surface (membrane) of the cultured cells. Particular apoptosis inhibitors contemplated by the present invention include, but are not limited to, the caspase-9 dominant negative (caspase-9-DN) mutant, bcl-2, baculovirus p35, caspase-9S (Seol,D. W. et al., *J. Biol. Chem.*, 274, 2072–2076 (1999)), crmA, z-VAD-fmk, z-DEVD-fmk, B-D-fmk, and z-YVAD-fmk, and variants therof. Preferably, the apoptosis inhibitor is one which acts upon one or more caspases located downstream in the intracellular cell death pathway of the cell, such as caspase-3. Optionally, the apoptosis inhibitor will, in an effective amount, decrease or reduce apoptosis in a cell culture by at least 50%, preferably, by at least 75%, more preferably, by at least 85%, and even more preferably, by at least 95%, as compared to a control cell culture which contains no such apoptosis inhibitor. Apoptosis or apoptotic activity in such cell cultures can be measured and determined using assays such as described herein. Optionally, the apoptosis inhibitor, in an effective amount, will enhance or increase yield of the recombinant protein of interest by at least 1-fold, and preferably by at least 2-fold, as compared to a control cell culture which contains no such apoptosis inhibitor. Optionally, the apoptosis inhibitor, in an effective amount, will enhance or increase transfection efficiency in transient transfections, preferably by at least 1-fold and more preferably, by at least 2-fold, as compared to a control cell culture which contains no such apoptosis inhibitor.

The term "protein of interest" refers to any protein which may be useful for research, diagnostic or therapeutic purposes. The protein of interest may comprise a mammalian protein or non-mammalian protein, and may optionally comprise a receptor or a ligand. Exemplary proteins of interest include, but are not limited to, molecules such as renin; a growth hormone, including human growth hormone and bovine growth hormone; growth hormone releasing factor; parathyroid hormone;. thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; members of the TNF and TNF receptor (TNFR) family, like tumor necrosis factor-alpha and -beta, CD40 ligand, Apo-2 ligand/TRAIL, DR4, DR5, DcR1, DcR2, DcR3, OPG, Fas ligand; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TG-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; thrombopoietin (TPO); interleukins (ILs), e.g., IL-1 to IL-10; superoxide dismutase; T-cell receptors; surface membrane proteins; decay accelerating factor; viral antigen such as, for example, a portion of the AIDS envelope, gp120; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and variants and/or fragments of any of the above-listed polypeptides; as well as antibodies against various protein antigens like CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac1, p150.95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C; an Apo-2L receptor such as Apo-2 (DR5), DR4, DcR1, DcR2, DcR3; and variants and/or fragments of the above-identified antibodies etc. In one embodiment of the invention, a protein of interest will comprise a protein which itself is capable of inducing apoptosis in mammalian or non-mammalian cells in vitro or in vivo, such as Apo-2 ligand/TRAIL, Fas ligand, or TNF-alpha.

"Isolated," when used to describe the various proteins of interest disclosed herein, means protein that has been identified and separated and/or recovered from a component of its natural environment. Contaminant components of its natural environment are materials that would typically interfere with research, diagnostic or therapeutic uses for the protein of interest, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the protein of interest's natural environment will not be present. Ordinarily, however, isolated protein will be prepared by at least one purification step.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordace with conventional practice.

As used herein, the expressions "cell", "cell line", and "cell culture" are used interchangeably and all such designations include progeny. Thus, the terms "transformants" and "transfectants" include the primary subject cell and cultures derived therefrom without regard for the number of transfers.

"Growth phase" of the cell culture refers to the period of exponential cell growth (the log phase) where cells are generally rapidly dividing. During this phase, cells are cultured for a period of time, usually between 1–4 days, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. During the growth phase, cells are cultured in nutrient medium containing the necessary additives generally at about 30–40° C., preferably about 37° C., in a humidified, controlled atmosphere, such that optimal growth is achieved for the particular cell line. Cells are maintained in the growth phase for a period of about between one and four days, usually between two to three days.

"Transition phase" of the cell culture refers to the period of time during which culture conditions for the production phase are engaged. During the transition phase environmental factors such as pH, ion concentration, and temperature may shifted from growth conditions to production conditions.

"Production phase" of the cell culture refers to the period of time during which cell growth has reached a plateau. During the production phase, logarithmic cell growth has ended and protein production is primary. During this period of time the medium is generally supplemented to support continued protein production and to achieve the desired protein product.

The term "expression" or "expresses" is used herein to refer to transcription and translation occurring within a host cell. The level of expression of a product gene in a host cell may be determined on the basis of either the amount of corresponding mRNA that is present in the cell or the amount of the protein encoded by the product gene that is produced by the cell. For example, mRNA transcribed from a product gene is desirably quantitated by northern hybridization. See, e.g., Sambrook et al., Molecular Cloning: A Laboratory Manual, pp. 7.3–7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein. See, e.g., Sambrook et al., Molecular Cloning: A Laboratory Manual, pp. 18.1–18.88 (Cold Spring Harbor Laboratory Press, 1989).

The terms "apoptosis" and "apoptotic activity" are used in a broad sense and refer to the orderly or controlled form of cell death in mammalian or non-mammalian cells that is typically accompanied by one or more characteristic cell changes, including condensation of cytoplasm, loss of plasma membrane microvilli, activation of caspase(s), segmentation of the nucleus, degradation of chromosomal DNA or loss of mitochondrial function. This activity can be determined and measured, for instance, by cell viability assays, FACS analysis, annexin V binding, or DNA electrophoresis such as is known in the art and described further herein.

II. The Methods of the Invention

Cells grown in cell culture may begin to lose viability within days of initiating the culture. Loss of cell viability can particularly be problematic when culturing cells in relatively large, batch scale cultures or bioreactors. For instance, CHO cells grown in batch culture can begin to lose cell viability as early as Day 4 after which a rapid decline in viability can continue until the culture is terminated. The mechanism by which such cultured cells die may be either through necrosis or apoptosis. Using TUNEL and Annexin/PI binding assays, Applicants discovered that approximately 80% of some CHO cells grown in batch culture may die by apoptosis rather than through necrosis. As described herein, Applicants have surprisingly found methods which allow a marked reduction of such apoptosis.

The methods disclosed in the present application have a variety of applications and improvements for recombinant protein production. First, by prolonging host cell viability in culture (and during fermentation), one skilled in the art can increase production and yield of the protein of interest. This can improve the efficiency of the cell culture run and result in marked cost savings. Further, Applicants have found the use of one or more apoptosis inhibitors in the methods of the invention may protect against potential adverse effects of agents like butyrate or TSA included in the cell culture. Also, the methods herein can enhance quality of the expressed and recovered protein of interest. The quality of the expressed and recovered protein of interest may be evaluated using techniques known in the art, such as SDS-PAGE, etc. The occurrence of cell death in recombinant cell cultures oftentimes results in the release of various active proteins from the dying cells, such as proteases [Lao, M., et al., *Cytotechnology*, 22: 43–52 (1996); Teige, M., et al., *J. Biotechnol.*, 34:101–105 (1994)], glycosidases such as sialidase or β-galactosidase [Gramer M. J. and Goochee C. F., *Biotechnol. Prog.*, 9:366–373 (1999)], or proline isomerase [Schmid, *Current Biology*, 5:933–944 (1995)]. These and other such proteins are often capable of degrading the product quality or function of the desired recombinant protein(s) being expressed, for instance, by undesired cleavage, carbohydrate modification (glycoprotein modification)[Wittwer A., and Howard, S. C., *Biochem.*, 29:4175–4180 (1990); Hart, *Curr. Op. Cell Biol.*, 4:1017–1023 (1992); Goochee, et al., *Bio/Technology*, 9:1347–1355 (1991)], or protein structure modification (such as folding or aggregation). By decreasing or inhibiting apoptosis in the cell culture, the present methods can decrease the number or presence of such adverse proteases in the culture media and protect the expressed protein of interest against proteolytic degradation.

The methods herein can further be employed to increase transfection efficiency and viability of cells during transfection. Reagents used in various transfection techniques, such as Lipofectamine or DMRIE-C (Gibco), can be relatively toxic to the cells when used in higher concentrations. The use of higher concentrations of transfection reagents, however, would be particularly helpful to achieve higher transfection efficiencies. The expression of apoptosis inhibitor and/or the addition of apoptosis inhibitor directly to the cell culture medium can be used to reduce or inhibit cell death even when such higher concentrations of a transfection reagent are selected. The use of apoptosis inhibitor in this manner can result in higher transfection efficiency and higher yield of the recombinant protein of interest.

The methods disclosed can be further used to express proteins of interest which are proteins that, themselves, induce apoptosis. Such proteins like Apo-2 ligand/TRAIL or Fas ligand, can trigger apoptosis when expressed in cells. The presence of apoptosis inhibitor(s), in accordance with the present methods, may block such apoptotic activity and allow for improved expression of the protein of interest.

In addition, the methods can be used to increase the viability of cells undergoing freezing/storage/thawing procedures. During these procedures generally cells can lose viability. The presence of apoptosis inhibitor(s) expressed in cells (or added to the cell culture media) can provide for increased cell viability and aid in reducing or eliminating the variability in cell viabilities between aliquots or vials of cells.

The methods according to the present invention are described in further detail below.

The DNA encoding the protein of interest may be obtained from a variety of sources, for instance, from any cDNA library prepared from tissue believed to possess its mRNA and to express it at a detectable level. The gene encoding the protein of interest may also be obtained from a genomic library or by oligonucleotide synthesis. Screening such a cDNA or genomic library with a selected probe may be conducted using standard procedures, such as described in Sambrook et al., *Molecular Cloning: A Laboratory Manual* (New York: Cold Spring Harbor Laboratory Press, 1989). An alternative means to isolate the gene encoding the protein of interest is to use PCR methodology [Sambrook et al., supra; Dieffenbach et al., *PCR Primer: A Laboratory Manual* (Cold Spring Harbor Laboratory Press, 1995)].

Various proteins of interest have been specifically referred to above and their respective gene sequences are generally known and publicly available.

Genes encoding various apoptosis inhibitors have also been described in the literature [see e.g., Clem R. J. et al., *Science*, 254, 1388–1390 (1991); Duan, H. et al., *J. Biol. Chemistry*, 271, 16720–16724 (1996); Pan, G. et al., *J. Biol. Chemistry*, 273, 5841–5845 (1998); Vaux, D. L. et al., *Science*, 258, 1955–1957 (1998); Tsujimoto et al., *Proc. Natl. Acad. Sci.*, 83:5214–5218 (1986)]. The methods of the present invention contemplate the use of a single apoptosis inhibitor-encoding gene as well as the use of a combination of two or more apoptosis inhibitor-encoding genes. Potentially, the expression of two or more types of apoptosis inhibitor(s) in a host cell may be beneficial in controlling apoptosis in the cell culture. One skilled in the art can monitor the quantity or amount of apoptosis inhibitor being expressed by the host cells, such as by a Western blot analysis using an antibody that recognizes the apoptosis inhibitor. The quantity or amount of apoptosis inhibitor, as well as the timing of its expression, can be regulated or monitored, for instance, by choosing a vector with an inducible promoter.

When selecting an apoptosis inhibitor for use in the claimed methods, those skilled in the art will appreciate that various apoptosis inhibitor molecules may act upon different intracellular components of the signaling pathway which leads to cell death. The pathways involved in cell death comprise a family of cysteine proteases, called caspases, that are related to the mammalian interleukin-1 beta converting enzyme (caspase-1) and to Ced-3, the product of a gene of C. elegans. It is believed that such caspase molecules can act at at least two different levels. Initiator caspases are typically "upstream" molecules that are activated in response to stimuli indicating that the cell has been stressed, damaged, or received some form of signal to initiate cell death by apoptosis. An example of such an upstream caspase is caspase-8. Initiator caspases can then, in turn, cleave and activate another family of "downstream" caspases, such as caspase-3. Depending upon the nature of the apoptotic stimulus as well as the cell type, only a portion of the signaling pathway may be involved in the signaling mechanism and execution of cell death. For example, certain apoptosis inhibitors, such as CrmA, are believed to act upon caspases, such as caspase-8, located upstream and are usually directly activated by death receptor binding to ligand. Other apoptosis inhibitors are believed to act upon other caspases located downstream in the intracellular signaling pathway. Thus, it is is presently believed that inhibitors of those molecule(s) that are effectively engaged (such as actively engaged in the signal transmission) in the cell death apparatus in a selected cell will be effective as apoptosis inhibitors, as described herein. Applicants do note, however, that those skilled in the art will understand that in such signaling pathways, there is point at which the cell is "committed" to cell death, and once the signaling pathway has transmitted a signal(s) to the point where the cell is committed to cell death, apoptosis inhibitor molecules, like those described herein, may not be effective in inhibiting or preventing the apoptosis of the "committed" cell.

The cytokine response modifier, CrmA, is a 38 kDa serpin identified from cowpox virus that has been reported to inhibit apoptosis in several systems [Gagliardini et al., Science, 263:826–828 (1994); Tewari et al., J. Biol. Chem., 270:3255–3260 (1995)]. CrmA has been evaluated as an inhibitor of caspase-1 and caspase-8 [Nicholson et al., Nature, 376:37–43 (1995); Zhou et al., J. Biol. Chem., 272:7797–7800 (1997)]. In some studies conducted by Applicants, it was observed that overexpression of CrmA in CHO dhfr+cells was unable to substantially delay cell death in the environment of a bioreactor. This result suggested that in this particular CHO cell system selected by Applicants, neither caspase-1 nor caspase-8 were actively involved in the cell death pathway of those particular cultured cells. Accordingly, to achieve the desired effects described herein, it is preferred to select an apoptosis inhibitor molecule which acts downstream in the selected host cell's cell death signaling pathway, but prior to the point where the cell has been committed to cell death.

The nucleic acids (e.g., cDNA or genomic DNA) encoding the protein of interest and the apoptosis inhibitor may be inserted into replicable vector(s) for expression. Various vectors are publicly available. The vector components generally include, but are not limited to, one or more of the following: a signal sequence, an origin of replication, one or more marker genes, an enhancer element, a promoter, and a transcription termination sequence, each of which is described below. Optional signal sequences, origins of replication, marker genes, enhancer elements and transcription terminator sequences that may be employed are known in the art and described in further detail in WO97/25428.

Techniques for inserting such genes into vectors are well known to the skilled artisan and such techniques can be accomplished without undue experimentation. Construction of suitable vectors can employ standard ligation techniques. Isolated plasmids or DNA fragments are cleaved, tailored, and re-ligated in the form desired to generate the plasmids required. Techniques known in the art may be employed. [See, e.g., Messing et al., Nucleic Acids Res., 9:309 (1981); Maxam et al., Methods in Enzymology, 65:499 (1980)].

The gene encoding the apoptosis inhibitor and the gene encoding the protein of interest may be inserted into a single vector (co-transfected), or be inserted into two separate or different vectors. Preferably, the respective genes are inserted into two separate vectors. Each such vector will typically contain a selection gene, also termed a selectable marker. Typical selection genes encode proteins that (a) confer resistance to antibiotics or other toxins, e.g., ampicillin, neomycin, puromycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 [Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 [Jones, Genetics, 85:12 (1977)].

In the methods employing a first vector comprising an apoptosis inhibitor gene and a second vector comprising a gene encoding the protein of interest, it is preferred that the first and second vector carry different selection markers. For example, a vector comprising the apoptosis inhibitor gene might carry a selection gene to confer ampicillin resistance while the vector comprising the gene encoding the protein of interest might carry a selection gene to confer methotrexate resistance.

Expression vectors usually also contain a promoter that is recognized by the host organism and is operably linked to the inserted nucleic acid sequence(s) described above. Promoters are untranslated sequences located upstream (5') to the start codon of a structural gene (generally within about 100 to 1000 bp) that control the transcription and translation of a particular nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to the encoding DNA by removing the promoter from the source DNA by restriction enzyme digestion and inserting the isolated promoter sequence into the vector.

Promoters suitable for use with prokaryotic and eukaryotic hosts are known in the art, and are described in further detail in WO97/25428.

Expression vectors that provide for the transient expression of DNA encoding the protein of interest may be employed. In general, transient expression involves the use of an expression vector that is able to replicate efficiently in a host cell, such that the host cell accumulates many copies of the expression vector and, in turn, synthesizes high levels of a desired protein encoded by the expression vector [Sambrook et al., supra]. Transient expression systems, comprising a suitable expression vector and a host cell, allow for the convenient positive identification of proteins encoded by cloned DNAs, as well as for the rapid screening of such proteins for desired biological or physiological properties.

Host cells are transfected or transformed with the above-described expression vectors for production of the protein of interest and cultured in nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell. As described above, the use of an apoptosis inhibitor gene (or adding an apoptosis inhibitor molecule directly to the culture media) may improve transfection efficiency. It is believed that use of such apoptosis inhibitor(s) will allow for use of increased amounts of transfection reagents, such as Lipofectamine or DMRIE-C (as described in the Examples below).

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with Agrobacterium tumefaciens is used for transformation of certain plant cells, as described by Shaw et al., Gene, 23:315 (1983) and WO 89/05859 published Jun. 29, 1989. In addition, plants may be transfected using ultrasound treatment as described in WO 91/00358 published Jan. 10, 1991. For mammalian cells without such cell walls, the calcium phosphate precipitation method of Graham and van der Eb, Virology, 52:456–457 (1978) can be employed. General aspects of mammalian cell host system transformations have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527–537 (1990) and Mansour et al., Nature, 336:348–352 (1988).

Suitable host cells for expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as E. coli. Various E. coli strains are publicly available, such as E. coli K12 strain MM294 (ATCC 31,446); E. coli X1776 (ATCC 31,537); E. coli strain W3110 (ATCC 27,325) and K5 772 (ATCC 53,635); Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41P disclosed in DD 266,710 published Apr. 12, 1989), Pseudomonas such as P. aeruginosa, and Streptomyces.

In addition to prokaryotes, eukaryotic microbes such as filamentous fungi or yeast are suitable. Saccharomyces cerevisiae is a commonly used lower eukaryotic host microorganism.

Suitable host cells may be derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFR (CHO, Urlaub and Chasin, Proc. Natl. Acad. Sci. USA, 77:4216 (1980)); dp12.CHO (EP 307,247 published Mar. 15, 1989), mouse sertoli cells (TM4, Mather, Biol. Reprod., 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

The selection of a particular apoptosis inhibitor to employ with a particular host cell and protein of interest can be made without undue experimentation by one of ordinary skill in the art.

Prokaryotic cells used to produce the protein of interest may be cultured in suitable culture media as described generally in Sambrook et al., supra. Particular forms of culture media that may be employed for culturing CHO are described further in the Examples below. Mammalian host cells used to produce the protein of interest may be cultured in a variety of culture media. Suitable culture conditions for mammalian cells are well known in the art (J. Immunol. Methods (1983)56:221–234) or can be easily determined by the skilled artisan (see, for example, Animal Cell Culture: A Practical ApDroach 2nd Ed., Rickwood, D. and Hames, B. D., eds. Oxford University Press, New York (1992)), and vary according to the particular host cell selected.

Examples of commercially available culture media include Ham's F10 (Sigma), Minimal Essential Medium ("MEM", Sigma), RPMI-1640 (Sigma), and Dulbecco's Modified Eagle's Medium ("DMEM", Sigma). In addition, any of the media described in Ham and Wallace,(1979) Meth. Enz., 58:44; Barnes and Sato,(1980) Anal. Biochem., 102:255; U.S. Pat. Nos. 4,767,704; 4,657,866; 4,927,762; 5,122,469 or 4,560,655; International Publication Nos. WO 90/03430; and WO 87/00195 may be used. Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. The necessary growth factors for a particular cell are readily determined empirically without undue experimentation, as described for example in *Mammalian Cell Culture* (Mather, J. P. ed., Plenum Press, N.Y. (1984), and Barnes and Sato, (1980) Cell, 22:649.

Other methods, vectors, and host cells suitable for adaptation to the synthesis of the protein of interest in recombinant vertebrate cell culture are described in Gething et al., *Nature*, 293:620–625 (1981); Mantei et al., *Nature*, 281:40–46 (1979); EP 117,060; and EP 117,058. In general, principles, protocols, and practical techniques for maximizing the productivity of mammalian cell cultures can be found in *Mammalian Cell Biotechnology: A Practical Approach*, M. Butler, ed. (IRL Press, 1991).

The amount of apoptosis inhibitor added directly, or admixed, to the culture media will depend on various factors, for instance, the type of apoptosis inhibitor molecule being employed, the type of host cell, culture conditions, etc. Determining the desired concentration of apoptosis inhibitor to be added to the culture media is within the skill in the art and can be ascertained empirically without undue experimentation. Preferably, an effective amount or desired concentration of apoptosis inhibitor added directly to the culture media is such that the apoptosis inhibitor penetrates into the host cell. The skilled artisan will readily appreciate that different apoptosis inhibitors may have different abilities to penetrate into the host cell, and therefore, one should choose a concentration which allows for such penetration into the host cell. There will typically be an upper range of concentration of apoptosis inhibitor which may not be desirable as the concentration approaches a range which is adverse or toxic to the host cells. As described in the Examples below, Applicants have found that z-VAD-fmk can inhibit apoptosis when added to cell cultures at a concentration of about 100 micromolar. A variety of apoptosis inhibitor compounds such as z-VAD-fmk, z-DEVD-fmk, B-D-fmk, and z-YVAD-fmk are available from vendors, such as Pharmingen and Enzyme Systems, Livermore, Calif.

The apoptosis inhibitor may be added directly into the culture media. The apoptosis inhibitor may be added at any point during the culturing of the cells. Optionally, the apoptosis inhibitor is added to the culture media at the beginning (at the time of initiating, day 0) of the cell culturing process. Preferably, such an apoptosis inhibitor would be added to the culture media during the culturing of the cells but prior to the point when induction of apoptosis occurs; typically, induction of apoptosis can be observed in large scale cell cultures on about day 3 or day 4 of the culture, and therefore, the apoptosis inhibitor will preferably be added prior to day 3 or day 4. Optionally, a desired quantity of apoptosis inhibitor is added throughout, or for the duration of, the cell culture, for instance, on a daily basis for the entire fermentation. As an example, for a 5 day culture, the apoptosis inhibitor could be added at day 0, and every 24 hours thereafter until the culture is terminated.

In one embodiment of the invention, the selected host cell is a CHO cell, preferably, a dp12.CHO cell, and the selected culture medium contains a basal medium component such as a DMEM/HAM F-12 based formulation (for composition of DMEM and HAM F12 media and especially serum free media, see culture media formulations in American Type Culture Collection Catalogue of Cell Lines and Hybridomas, Sixth Edition, 1988, pages 346–349) (the formulation of medium as described in U.S. Pat. No. 5,122,469 are particularly appropriate) with modified concentrations of some components such as amino acids, salts, sugar, and vitamins, and optionally containing glycine, hypoxanthine, and thymidine; recombinant human insulin, hydrolyzed peptone, such as Primatone HS or Primatone RL (Sheffield, England), or the equivalent; a cell protective agent, such as Pluronic F68 or the equivalent pluronic polyol; Gentamycin; and trace elements. Preferably, the selected cell culture media is serum free.

The proteins of interest may be produced by growing the host cells under a variety of cell culture conditions. For instance, cell culture procedures for the large or small scale production of proteins are potentially useful within the context of the present invention. Procedures including, but not limited to, a fluidized bed bioreactor, hollow fiber bioreactor, roller bottle culture, or stirred tank bioreactor system may be used, in the later two systems, with or without microcarriers, and operated alternatively in a batch, fed-batch, or continuous mode.

In a preferred embodiment, the cell culture of the present invention is performed in a stirred tank bioreactor system and a fed batch culture procedure is employed. In the preferred bioreactor system, the size of the bioreactors are sufficiently large to produce the desired amount of protein of interest, such as 1,000 Liter or 12,000 Liter sizes, but are not limited to such sizes as much smaller (i.e., 2 Liter, 400 Liter) or larger (i.e., 25,000 Liter, 50,000 Liter) bioreactor vessels may be appropriate. In the preferred fed batch culture, the mammalian host cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernate is not removed from the culturing vessel during the process but at the termination of the culture process (in perfusion culturing, the cells are restrained in the culture by, e.g., filtration, encapsulation, anchoring to microcarriers etc. and the culture medium is continuously or intermittently introduced and removed from the culturing vessel).

Further, the cultured cells may be propagated according to any scheme or routine that may be suitable for the particular host cell and the particular production plan contemplated. Therefore, the present invention contemplates a single step or multiple step culture procedure. In a single step culture, the host cells are inoculated into a culture environment and the method steps of the instant invention are employed during a single production phase of the cell culture. Alternatively, a multi-stage culture is envisioned. In the multi-stage culture, cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

According to a preferred aspect of the invention, fed batch or continuous cell culture conditions are devised to enhance growth of the mammalian cells in the growth phase of the cell culture. In the growth phase, cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30 to 38° C. and preferably about 37° C. and a suitable $dO_2$ is between 5–90% of air saturation.

At a particular stage the cells may be used to inoculate a production phase or step of the cell culture. Alternatively, as described above, the production phase or step may be continuous with the inoculation or growth phase or step.

According to the present invention, the cell culture environment during the production phase of the cell culture is controlled. According to the steps of the presently disclosed methods, the concentration of apoptosis inhibitor in the culture medium can be manipulated such that the desired content and quality of the protein of interest is achieved and maintained in the resulting cell culture fluid. In a preferred aspect, the production phase of the cell culture is preceded by a transition phase of the cell culture in which expression of or addition of apoptosis inhibitor(s) for the production phase of the cell culture are engaged. Concentrations of apoptosis inhibitor(s) are preferably monitored in connection with other process parameters such as the osmolality of the production phase since osmolality can affect the cell specific productivity.

In any of the above-described methods, it is contemplated that it may be desirable to include a desired amount of agent like butyrate or TSA in the cell culture medium. Various forms of butyrate and its salts are known in the art, such as butyric acid and sodium butyrate, and are publicly available from sources such as Sigma Chemical Co. Butyrate has been reported in the literature to enhance the productivity and protein expression of cell cultures [Arts et al., *Biochem J.*, 310:171–176 (1995); Gorman et al., *Nucleic Acids Res.*, 11:7631–7648 (1983); Krugh, *Mol. Cell. Biochem.*, 42:65–82 (1982); Lamotte et al., *Cytotechnology*, 29:55–64 (1999); Chotigeat et al., *Cytotechnology*, 15:217–221 (1994)]. Trichostatin A (TSA) is an inhibitor of histone deacetylase and may act similarly to butyrate in enhancing the productivity and protein expression in cell cultures [Medina et al.,*Cancer Research*, 57:3697–3707 (1997)]. Although butyrate has some positive effects on protein expression, it is also appreciated in the art that at certain concentrations, butyrate can induce apoptosis in the cultured cells and thereby decrease viability of the culture as well as viable cell density [Hague et al., *Int. J. Cancer*, 55:498–505 (1993); Calabresse et al., *Biochim. Biophys. Res. Comm.*, 195:31–38 (1993); Fillipovich et al., *Biochim. Biophys. Res. Comm.*, 198:257–265 (1994); Medina et al., *Cancer Research*, 57:3697–3707 (1997)]. In the methods of the present invention, a desired amount of butyrate or TSA may be added to the cell culture at the onset of the production phase and more preferably, may be added to the cell culture after a temperature shift has been implemented. Butyrate or TSA can be added in a desired amount determined empirically by those skilled in the art, but preferably, butyrate is added to the cell culture at a concentration of about 1 to about 25 mM, and more preferably, at a concentration of about 1 to about 6 mM.

Expression of the protein of interest may be measured in a sample directly, for example, by ELISA, conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe. Various labels may be employed, most commonly radioisotopes, and particularly $^{32}p$. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like.

Antibodies useful for immunohistochemical staining and/ or assay of sample fluids may be either monoclonal or polyclonal, and may be prepared in any mammal.

It is usually necessary to recover or purify the protein of interest from recombinant cell proteins or polypeptides to obtain preparations that are substantially homogeneous. As a first step, the culture medium or lysate may be centrifuged to remove particulate cell debris. The protein of interest thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cationexchange resin such as DEAE; chromatography on protein A Sepharose columns, chromatofocusing; SDS-PAGE; ammonium sulfate precipitation; and gel filtration using, for example, Sephadex G-75.

The recovered or purified protein of interest will typically be analyzed by one or more of the following methods: SDS-polyacrylamide gel electrophoresis, HPLC, mass spectrometry of a tryptic digest, glycoprotein analysis and activity assays.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, unless otherwise indicated, is the American Type Culture Collection, Manassas, Va.

Example 1

Apoptotic Cell Death in Bioreactors

Serum free adapted, CHO (dhfr+) cells were scaled up and seeded at 1 million cells/ml in 2 liter bioreactors (n=2).

The cell culture media was a serum-free DMEM/Ham F-12 based medium containing recombinant human insulin and trace elements. Cells were grown at 37° C. with agitation set at 275 rpm. pH was kept at 7.2 and was automatically adjusted throughout the experiment. Bioreactors were sparged with a mixture of oxygen and air. This is a model system that mimics the conditions during large-scale production of therapeutic proteins.

Samples were taken every day to measure the following parameters: cell viability, caspase activity (Clontech), DNA fragmentation and annexin/PI binding (Chemicon). FIG. 1A shows cell viability as determined (by Trypan blue exclusion) over the course of 5 days. FIG. 1B shows that loss of cell viability over the 5 day period in culture was the result of apoptosis.

Example 2

Effects of Caspase-9 Dominant Negative in CHO Cells

Expression construct: C-terminal FLAG-tagged caspase-9-dominant negative ("caspase-9-DN") cDNA (Duan, H. et al., *J. Biol. Chemistry*, 271, 16720–16724 (1996); Pan, G. et al., *J. Biol. Chemistry*, 273, 5841–5845 (1998)) was subcloned in a mpsv splice donor as further described: 2 ug of mpsv vector (Genentech, Inc.) was digested with 5 U of EcoRI and 5 U of BamHI (Boehringer Mannheim) and 2 ul of buffer A (Boehringer Mannheim) in a total volume of 20 ul for 1 hour at 37° C. 2 ug of caspase-9-DN/pcDNA3 construct was digested with 5 U of HindIII and 5 U of XbaI with 2 ul of buffer B (Boehringer Mannheim) in a total volume of 20 ul for 1 hour at 37° C. After incubation, 1 ul of 1 mM dNTPs (Clontech) and 0.2 U of Klenow polymerase (Boehringer Mannheim) was added to each reaction and the incubation was continued for an additional 15 minutes at 37° C.

Aliquots of each digest were analyzed by 1% agarose gel electrophoresis. 1.2 kbp caspase-9-DN cDNA and linearized 9.7 kbp mpsv vector were cut out of the gel and the DNA was purified using GeneClean (Bio101, Inc.) according to the manufacturer's instructions.

Ligation of caspase-9-DN and mpsv vector: 50 ng of vector and 42 ng of insert were ligated in 10 ul 2×ligation buffer and 1 ul T4 DNA ligase in 20 ul total volume at room temperature for 5 minutes (Boehringer Mannheim).

Transformation: MaxEfficiency DH5alfa competent cells (Gibco BRL) were transformed with 2 ul ligation mixture according to manufacturer's instructions. Transformed cells were then plated on carbenicillin containing LB plates. Colonies were randomly picked and analyzed by restriction digest to identify a colony containing the correct construct. Colony #30 was chosen for further work.

Transfection: E25 producing CHO DP12 cells [as designated throughout the present application, "E25" refers to the transfected CHO cells expressing a humanized monoclonal antibody against human IgE; see Presta et al., *J. Immunology*, 151:2623–2632 (1993)] were chosen for transfection with mpsv/caspase-9-DN and mpsv vector. Transfection was done using LipofectAMINE Plus Reagent (Gibco BRL) and was performed as follows:

E25 cells grown in suspension were plated on 60 mm tissue culture dishes (1 million cells/plate) 24 hours prior to transfection in a serum-containing medium. DNA for transfection was quantified spectrophotometrically. Two ug of DNA was mixed with 250 ul serum-free medium and 8 ul of Plus reagent and incubated for 15 minutes at room temperature. Twelve ul of reagent were mixed with 250 ul of serum-free medium and directly added to the mixture followed by incubation for 15 minutes at room temperature. The medium on top of the cells was replaced with 5 ml of fresh serum-free medium and the transfection mixture was added to the dish. Three hours post-transfection, medium was replaced with a serum-containing medium. 24 hours post-transfection, each transfected dish was split into 5 dishes and a selection pressure was applied by the addition of 5 ug/ml puromycin. Transfected clones (resistant to puromycin) began to appear about two weeks after transfection. Several clones were chosen for analysis of caspase-9-DN expression by Western blotting.

Western blot analysis: Selected clones were picked and transferred into a 24 well plate. When confluent, cells from each well were rinsed with PBS and lysed for 3 minutes in 100 ul lysis buffer (3% NP 40 in PBS). The lysates were centrifuged for 3 minutes at 12,000×g. Supernatant was collected, mixed with an equal volume of reducing 2×SDS loading buffer (Novex) and boiled for 3 minutes. Samples were stored at −20° C. Aliquots of the lysates were subjected to a protein assay to determine the total protein concentration using Micro BCA Protein Assay Reagent Kit (Pierce).

Aliquots of lysates corresponding to 3 ug of total protein were loaded on a 10% SDS Tris-glycine gel (Novex) and ran for 1½ hours. Proteins were transferred to an Immobilon-P transfer Membrane according to manufacturer's directions.

The membrane was probed with rabbit anti-caspase-9 serum (Pharmingen) followed by HRP conjugated goat-anti-rabbit antiserum and developed using ECL Western Blotting detection Reagent (Amersham). Clones with high as well as low expression of caspase-9-DN (clones 2 and 14) were selected for further characterization. See FIG. 2.

Induction of apoptosis with staurosporine: Clones 2 and 14 expressing low and high levels of caspase-9-DN (respectively) were adapted to growth in serum-free medium in spinners. Clones were seeded in spinners at 1 million cells/ml and an apoptosis inducing agent, staurosporine (Sigma), was added at 1 uM final concentration. Aliquots of culture were analyzed for apoptosis by several assays: annexin/PI (Chemicon) to measure the % of apoptotic cells and by caspase-3 activity (Clontech) according to manufacturer's instructions. See FIGS. 3 and 4.

The effect of caspase-9-DN expression on viability in 2 liter bioreactors: Serum free adapted, caspase-9-DN expressing clones 2 and 14, a vector control and untransfected E25 cells were scaled up and seeded at 1 million cells/ml in 2 liter bioreactors (n=2). The cell culture media was a serum-free DMEM/Ham F-12 based medium containing recombinant human insulin and trace elements. Cells were grown at 37° C. with agitation set at 275 rpm. pH was kept at 7.2 and was automatically adjusted throughout the experiment. Bioreactors were sparged with a mixture of oxygen and air. This is a model system that mimics the conditions during large-scale production of therapeutic proteins.

Samples were taken every day to measure the following parameters: cell viability, cell density, apoptosis, caspase-3 activation, glucose consumption, osmolality, lactate production and E25 titers. See FIGS. 5–8.

The results show stable expression of caspase-9-DN in CHO cells expressing E25. The stable expression resulted in a resistance of the cells to an apoptosis inducing agent, staurosporine. The resistance was proportional to the expression levels of caspase-9-DN. In the environment of a bioreactor, the high expessing clone 14 showed dramatically prolonged viability and viable cell count compared with the lower expressing clone 2, which showed only a moderate prolongation of viability and viable cell count. Prolongation of viability is reflected in the delayed onset of caspase-3 activation in clone 14 compared with the controls. Unexpected results were obtained in the assay for the amount of E25 antibody secreted into the medium. Although caspase-9-DN clone 14 resulted in superior prolongation of viability in the bioreactor than clone 2, clone 14 produced less protein of interest (E25 antibody). The data suggested that high expression of apoptosis inhibitor may not concomitantly delay cell death and increase yield of the protein of interest.

However, in another 2 liter bioreactor assay, a cell culture was similarly run as described above with the exception of the following changes: (1) caspase-9-expressing clone 14 and E25 control cells were seeded at 1 million cells/ml; and (2) the medium was a serum free, concentrated medium (used to enhance nutrient supply in the medium) based on DMEM/Ham F-12 with insulin and trace elements. The cell cultures were grown for 1 day at 37° C. and then temperature shifted to 33° C. On the third day, the pH of the cultures was shifted from pH 7.15 to pH 7.0, and the cultures were fed with concentrated DMEM/Ham F-12, glucose and protein hydrolysate medium in order to supply enough nutrients to support optimal growth.

The results are shown in FIGS. 17 and 18. As illustrated in the graphs, caspase-9-DN expression resulted in prolongation of viability and increase in viable cell densities, as well as higher titers of the protein of interest (E25 antibody) as compared to the control. Under the conditions of fed-batch culture where nutrients were not limiting, the data showed that prolongation of viability and increase in viable cell densities were accompanied by a marked increase in product titer.

Example 3

Effects of Caspase Inhibitor z-VAD-fmk on Apoptosis

CHO (dhfr+) cells grown in suspension were seeded at 1 million cells/ml in 60 mm tissue culture dishes. The cell culture media was a serum-free DMEM/Ham F-12 based medium containing recombinant human insulin and trace elements. Viability of the culture on day 0 was 96%. Two plates were analyzed each day for viability by Trypan Blue exclusion and by annexin/PI binding (Clontech) and for viable cell density. The experiment was carried out for 10 days. A chemical inhibitor of caspases, z-VAD-fmk (Enzyme Systems Products) was dissolved in DMSO to make a 100 mM (1000x) stock and 4 ul was added to a 60 mm dish containing 4 ml of culture. The inhibitor was added 48 hours after the start of the experiment (prior to the onset of apoptosis) and a new aliquot of the z-VAD-fmk inhibitor was added every 24 hours. Controls were cultures without any addition and cultures with the addition of DMSO only.

The results are shown in FIGS. 9–10.

The chemical compound, z-VAD-fmk, is a caspase inhibitor and when added to the culture at 100 uM concentration, resulted in an inhibition of caspase-3 activity and prolongation of cell viability.

Example 4

Expression of Baculovirus p35 in CHO Cells

Expression construct: The baculovirus p35 cDNA (Beidler, D. et al., *J. Biol. Chemistry*, 270, 16526–16528 (1995); Clem, R. J. et al., *Science*, 254, 1388–1390 (1991)) was subcloned from a pcDNA3 vector (Invitrogen) into a CPC splice donor vector as follows: 2 ug of CPC vector (Genentech, Inc.) was linearized by digestion in 25 ul containing 7 U of EcoRI and 7 U of XbaI in High buffer (Boehringer Mannheim) for 2 hours at 37° C. Baculovirus p35 cDNA was cut out of the pcDNA 3 vector (Invitrogen) with the same restriction enzymes. An aliquot of each reaction was analyzed by electrophoresis in 1% agarose gel containing ethidium bromide. Bands corresponding to the linearized CPC vector (9.7 kbp) and p35 cDNA (0.9 kbp) were cut out of the gel and isolated using GeneClean (Bio 101, Inc.) according to manufacturer's instructions.

Ligation: 50 ng of vector and 25 ng of p35 cDNA were mixed with 10 ul of T4 ligation buffer and 1 ul T4 DNA ligase (Rapid DNA Ligation Kit, Boehringer Mannheim) in 20 ul total reaction volume. The reaction was incubated for 5 minutes at room temperature.

Transformation: 100 ul of Max Efficiency DH5alfa Competent cells (Boehringer Mannheim) were mixed with 2 ul of ligation mixture and incubated on ice for 30 minutes. Cells were heat-shocked for 45 seconds at 42° C. followed by incubation on ice for 2 minutes. 0.9 ml of LB medium was added to the cells and incubated for 1 hour at 37° C. with agitation. 100 ul of transformed cells were plated on LB agar plate with carbenicillin. Four clones were randomly picked and were grown overnight in 4 ml of LB+carbenicillin. The plasmid was isolated from these colonies using QIAprep Spin Miniprep Kit (Qiagen) according to manufacturer's instructions. Isolated plasmids were subjected to an analytical digest to confirm the correct construct.

Expression of baculovirus p35 in CHO cells: CHO (dhfr+) cells grown in a DMEM/Ham F-12 media containing 2% fetal bovine serum (Gibco), recombinant human insulin and trace elements were plated 48 hours prior to transfection at 2 million cells/100 m tissue culture dish. LipofectAMINE Plus Reagent (Gibco BRL) was used for transfection and was performed according to manufacturer's instructions. CHO cells were transfected with a p35 /CPC construct and CPC vector alone as a control. One transfected plate of each type was harvested 24 hours after transfection to assay the level of p35 expression in transient transfectants (Western blotting using anti-p35 rabbit polyclonal serum at 1:1000 dilution). Other tranfected plates were grown further and selection pressure (5 ug/ml puromycin) was applied 48 hours post-transfection. About two weeks later colonies resistant to puromycin developed and were adapted to serum free growth and scaled up for further analysis.

The effect of p35 expression on viability in 2 liter bioreactors: The serum free adapted clone expressing p35 and a vector control were scaled up and seeded at 1 million cells/ml in 2 liter bioreactors (n=2). The cell culture media was a serum-free DMEM/Ham F-12 based medium containing recombinant human insulin and trace elements. Cells were grown at 37° C. with agitation set at 275 rpm. pH was kept at 7.2 and was automatically adjusted throughout the experiment. Bioreactors were sparged with a mixture of oxygen and air. This is a model system that mimics the conditions during large-scale production of therapeutic proteins. Samples were taken every day to measure the following parameters: cell viability, cell density, apoptosis, caspase-3 activation, glucose consumption, osmolality and lactate production.

The results are shown in FIGS. 11–12.

The results indicate that the apoptosis inhibitor, baculovirus p35, when expressed in CHO cells results in prolongation of viability in the environment of the bioreactor.

Example 5

Increased Transfection Efficiency and Expression of E25 Antibody in Transient Transfections Using Caspase-9-DN Serum free adapted CHO DP12 cells were seeded at 1.5 million cells/ml in untreated 12 well tissue culture plates in medium based on DMEM/HAM F-12 with modified concentrations of some components and containing recombinant human insulin, trace elements and serum. Transfection was performed using DMRIE-C (Gibco BRL) according to manufacturer's instructions. Caspase-9-DN expressing clone 14 was transfected next to controls which were CHO DP12 cells and E25 cells (CHO DP12, expressing E25).

Red shifted GFP expressing vector (Quantum Biotechnologies Inc.) was co-transfected with a DNase expressing vector [Shak, S. et al., (1990), *Proc Natl. Acad. Sci USA*, 87:9188–9192)]. 24 hours post-transfection, propidium iodide was added to an aliquot of the culture and total and viable transfection efficiencies were assayed by flow cytometry on FACSCalibur (Becton Dickinson). Five days after transfection, a sample of the medium was subjected for DNase titer analysis using ELISA.

The data indicated (FIG. 13) that transfection reagent, in our experiment DMRIE-C, can be toxic to cells when used at higher concentrations (above 6 ul). In FIG. 14, caspase-9-DN clone 14 shows (in all concentrations of DMRIE-C tested) higher total and viable transfection efficiencies than controls. The transfection efficiency of clone 14 increased with the amount of transfection reagent and reached maximum at 12 ul of DMRIE-C, at which concentration both controls already started to show a decrease in transfection efficiency. It is possible that transfection efficiency of clone 14 will increase even further when higher than currently tested amount of DMRIE-C is used. The increase in transfection efficiency of clone 14 was reflected in the specific productivity (DNase titer/total LDH) of the culture and in DNase titer (FIGS. 15, 16), both of which were increased up to four-fold compared with the controls.

Example 6

Effect of Caspase 9-DN Expression on Viability and Viable Cell Number After Thawing a Frozen Culture $2 \times 10^7$ cells of caspase-9-DN expressing clone 14 and E25 control cells were frozen in a freezing medium (1 g/L methylcellulose in modified DMEM/Ham F-12 and 10% DMSO) and stored at $-80°$ C. for an extended period of time. On the day of the experiment, vials of frozen cells were taken out of the freezer, thawed at 37° C. and added to a spinner with a pre-warmed growth medium (modified DMEM/Ham F-12). Cells were cultured for 8 days and assayed for viability and viable cell density.

The results are shown in FIGS. 19 and 20. The results indicate that caspase-9-DN expressing cells maintained higher viability and viable cell count than the control E25 cells. Thus, expression of caspase-9-DN in the CHO cells had a beneficial effect on viability and viable cell densities upon thawing the frozen cell cultures.

Example 7

Caspase-9-DN Expressing Cells Show Resistance to Butyrate

The following study was conducted to examine whether caspase-9-DN expression affects resistance of the cells to potential adverse effects of butyrate.

Caspase-9-DN expressing clone 14 and E25 control cells were seeded at $1 \times 10^6$ cells/ml in 60 mm tissue culture dishes. Each dish contained 4 ml of culture medium. Cultures were grown at 37° C. in concentrated medium based on DMEM/Ham F-12 with insulin and trace elements. Cultures were temperature shifted to 33° C. on the second day and butyrate was added on the third day at varying final concentrations (0, 1, 2, 3, 5, 10 mM) (n=2). Viability of the cultures and titers were assayed daily.

The results are shown in FIGS. 21 and 22. The results showed that E25 control cells lose viability more rapidly than caspase-9-DN expressing cells (see FIG. 21, day 7 and day 9). This is reflected in the titers of protein of interest. Titers shown in FIG. 22 indicate that caspase-9-DN cells gave higher titers than 0 butyrate addition in cultures with 1 ,2 ,3 and 5 mM butyrate. On the other hand, titers of E25 controls improved with only 1 and 2 mM butyrate. The results suggest that caspase-9-DN expression protects cells from adverse effects of butyrate and can result in extended viability and higher titers.

What is claimed is:

1. A method of making recombinant proteins using one or more apoptosis inhibitors, comprising the steps of:
   (a) providing a vector comprising a gene encoding caspase-9 dominant negative protein,
   (b) providing a vector comprising a gene encoding a protein of interest,
   (c) providing a Chinese hamster ovary (CHO) host cell,
   (d) transforming or transfecting the host cell with the vector of steps (a) and (b),
   (e) providing cell culture media,
   (f) culturing the transformed or transfected host cell in the cell culture media under conditions sufficient for expression of the protein of interest and the caspase-9 dominant negative protein, and optionally
   (g) recovering or purifying the protein of interest from the host cell and/or the cell culture media.

2. The method of claim 1 further comprising the step of admixing an additional apoptosis inhibitor into the cell culture media in steps (e) or (f).

3. The method of claim 1 wherein the vector of step (a) and the vector of step (b) are the same vector.

4. The method of claim 1 wherein the vectors of steps (a) and (b) are two separate vectors.

5. The method of claim 4 wherein the vectors of steps (a) and (b) comprise different antibiotic resistance selection markers.

6. The method of claim 1 wherein the host cells are cultured under conditions for transient expression of the protein of interest.

7. The method of claim 1 wherein the protein of interest comprises a protein which is capable of inducing apoptosis in a mammalian or non-mammalian cell.

8. The method of claim 1 wherein said cell culture media is serum-free media.

9. The method of claim 1 wherein said cell culture media comprises butyrate.

10. The method of claim 1 wherein after step (f), the host cell(s) and/or cell culture media is frozen and subsequently thawed.

11. A method of making recombinant proteins using one or more apoptosis inhibitors, comprising the steps of:
   (a) providing a vector comprising a gene encoding a protein of interest,
   (b) providing a Chinese hamster ovary (CHO) host cell comprising a gene encoding caspase-9 dominant negative protein, (c) transforming or transfecting the host cell with the vector of step (a), (d) providing cell culture media, (e) culturing the transformed or transfected host cell in the cell culture media under conditions sufficient for expression of the protein of interest and the caspase-9 dominant negative protein and optionally (f) recovering or purifying the protein of interest from the host cell and/or cell culture media.

12. The method of claim 11 wherein the gene encoding the caspase-9 dominant negative protein is stably integrated into the genome of the host cell.

13. The method of claim 11 further comprising the step of admixing an additional apoptosis inhibitor molecule into the cell culture media in steps (d) or (e).

14. The method of claim 11 wherein said cell culture media comprises butyrate.

15. The method of claim 11 wherein after step (e), the host cell(s) and/or cell culture media is frozen and subsequently thawed.

16. A method of making recombinant proteins using one or more apoptosis inhibitors, comprising the steps of:

(a) providing a vector comprising a gene encoding a protein of interest, (b) providing a Chinese hamster ovary (CHO) host cell, (c) transforming or transfecting the host cell with the vector of step (a), (d) providing cell culture media, (e) providing an amount of caspase inhibitor z-VAD-fmk, (f) admixing the caspase inhibitor into the cell culture media, (g) culturing the host cell in the cell culture media under conditions sufficient for expression of the protein of interest, and optionally (h) recovering or purifying the protein of interest from the host cell and/or the cell culture media.

17. The method of claim 16 wherein after step (g), the host cell(s) and/or cell culture media is frozen and subsequently thawed.

18. A method of increasing yield of a protein of interest in a cell culture, comprising the steps of:

(a) providing a vector comprising a gene encoding caspase-9 dominant negative protein, (b) providing a vector comprising a gene encoding a protein of interest, (c) providing a Chinese hamster ovary (CHO) host cell, (d) transforming or transfecting the host cell with the vector of steps (a) and (b), (e) providing cell culture media, (f) culturing the transformed or transfected host cell in the cell culture media under conditions sufficient for expression of the protein of interest and an amount of the caspase-9 dominant negative protein which is effective in increasing yield of the protein of interest, and optionally (g) recovering or purifying the protein of interest from the host cell and/or the cell culture media.

19. The method of claim 18 wherein said cell culture media is serum-free media.

20. The method of claim 18 wherein after step (f), the host cell(s) and/or cell culture media is frozen and subsequently thawed.

21. A method of prolonging host cell viability in a cell culture, comprising the steps of:

(a) providing a vector comprising a gene encoding caspase-9 dominant negative protein, (b) providing a vector comprising a gene encoding a protein of interest, (c) providing a Chinese hamster ovary (CHO) host cell, (d) transforming or transfecting the host cell with the vector of steps (a) and (b), (e) providing cell culture media, (f) culturing the transformed or transfected host cell in the cell culture media under conditions sufficient for expression of the protein of interest and an amount of caspase-9 dominant negative protein which is effective for prolonging viability of the host cells in the cell culture, and optionally (g) recovering or purifying the protein of interest from the host cell and/or the cell culture media.

* * * * *